United States Patent
Prost et al.

(10) Patent No.: US 9,623,015 B2
(45) Date of Patent: Apr. 18, 2017

(54) COMBINATION OF AN ANTI-CANCER AGENT SUCH AS A TYROSINEKINASE INHIBITOR AND A STAT5 ANTAGONIST, PREFERABLY A THIAZOLIDINEDIONE, FOR ELIMINATING HEMATOLOGIC CANCER STEM CELLS IN VIVO AND FOR PREVENTING HEMATOLOGIC CANCER RELAPSE

(71) Applicant: Commissariat à L'Energie Atomique et aux Energies Alternatives (CEA), Paris (FR)

(72) Inventors: Stéphane Prost, Malabry (FR); Marek Kirszenbaum, Vanves (FR); Mikael Le Dantec, Paris (FR); Philippe Rousselot, Paris (FR); Philippe Leboulch, Charlestown, MA (US)

(73) Assignee: Commissariat à L'Energie Atomique et aux Energies Alternatives (CEA), Paris (FR)

( * ) Notice: Subject to any disclaimer, the term of this patent is extended or adjusted under 35 U.S.C. 154(b) by 0 days.

(21) Appl. No.: 14/440,001

(22) PCT Filed: Nov. 5, 2013

(86) PCT No.: PCT/IB2013/002583
§ 371 (c)(1),
(2) Date: Apr. 30, 2015

(87) PCT Pub. No.: WO2014/068397
PCT Pub. Date: May 8, 2014

(65) Prior Publication Data
US 2015/0265588 A1    Sep. 24, 2015

Related U.S. Application Data

(60) Provisional application No. 61/794,367, filed on Mar. 15, 2013, provisional application No. 61/722,633, filed on Nov. 5, 2012.

(51) Int. Cl.
*A61K 31/4439* (2006.01)
*A61K 31/506* (2006.01)
*A61K 45/06* (2006.01)
*A61K 31/404* (2006.01)
*A61K 31/426* (2006.01)
*A61K 31/427* (2006.01)
*A61K 31/496* (2006.01)
*A61K 31/5025* (2006.01)
*A61K 31/517* (2006.01)
*A61K 31/519* (2006.01)
*A61K 31/5377* (2006.01)

(52) U.S. Cl.
CPC ........ *A61K 31/4439* (2013.01); *A61K 31/404* (2013.01); *A61K 31/426* (2013.01); *A61K 31/427* (2013.01); *A61K 31/496* (2013.01); *A61K 31/506* (2013.01); *A61K 31/5025* (2013.01); *A61K 31/517* (2013.01); *A61K 31/519* (2013.01); *A61K 31/5377* (2013.01); *A61K 45/06* (2013.01)

(58) Field of Classification Search
CPC .................. A61K 31/4439; A61K 31/506
USPC .................................................. 514/252.18
See application file for complete search history.

(56) References Cited

U.S. PATENT DOCUMENTS

| | | |
|---|---|---|
| 4,287,200 A | 9/1981 | Kawamatsu et al. |
| 4,340,605 A | 7/1982 | Kawamatsu et al. |
| 4,438,141 A | 3/1984 | Kawamatsu et al. |
| 4,444,779 A | 4/1984 | Kawamatsu et al. |
| 4,461,902 A | 7/1984 | Kawamatsu et al. |
| 4,572,912 A | 2/1986 | Yoshioka et al. |
| 4,582,839 A | 4/1986 | Meguro et al. |
| 4,687,777 A | 8/1987 | Meguro et al. |
| 4,703,052 A | 10/1987 | Eggler et al. |
| 4,725,610 A | 2/1988 | Meguro et al. |
| 4,775,687 A | 10/1988 | Meguro et al. |
| 4,812,570 A | 3/1989 | Meguro et al. |
| 4,873,255 A | 10/1989 | Yoshioka et al. |
| 4,897,393 A | 1/1990 | Iijima et al. |
| 4,897,405 A | 1/1990 | Alessi et al. |
| 4,918,091 A | 4/1990 | Cantello et al. |
| 4,948,900 A | 8/1990 | Iijima et al. |
| 5,002,953 A | 3/1991 | Hindley |
| 5,061,717 A | 10/1991 | Clark et al. |

(Continued)

FOREIGN PATENT DOCUMENTS

| | | |
|---|---|---|
| EP | 0008203 A1 | 2/1980 |
| EP | 0139421 A1 | 5/1985 |

(Continued)

OTHER PUBLICATIONS

Nguyen et al. Clin. Cancer Res. (2011), v.17, p. 3219-3232.*
Barnes et al., Cell cycle, May 2006, 2862-2866.
Berria, R., et al. Reduction in hematocrit and hemoglobin following pioglitazone treatment is not hemodilutional in Type II diabetes mellitus. Clin Pharmacol Ther 82, 275-281 (2007).
Bonnet, D., Dick, J. Human acute myeloid leukemia is organized as a hierarchy that originates from a primitive hematopoietic cell. Nat Med 3, 730-737 (1997).
Chomel, J. C., et al. Leukemic stem cell persistence in chronic myeloid leukemia patients with sustained undetectable molecular residual disease. Blood 118, 3657-3660 (2011).

(Continued)

*Primary Examiner* — Yong Chu
(74) *Attorney, Agent, or Firm* — Nelson Mullins Riley & Scarborough LLP; Jane E. Remillard, Esq.; Cynthia L. Kanik

(57) ABSTRACT

Provided are methods for eliminating hematologic cancer stem cells in vivo, and thus preventing cancer relapse. The methods comprise a Signal Transducer and Activator of Transcription 5 (STAT5) antagonist (e.g., a PPARγ agonist) after the patient has had ana initial course of treatment with an anti-cancer agent (e.g., a TKI), to eliminate residual cancer stem cells which cause relapse.

28 Claims, 17 Drawing Sheets

(56) References Cited

U.S. PATENT DOCUMENTS

| | | | |
|---|---|---|---|
| 5,120,754 | A | 6/1992 | Clark et al. |
| 5,132,317 | A | 7/1992 | Cantello et al. |
| 5,194,443 | A | 3/1993 | Hindley |
| 5,223,522 | A | 6/1993 | Clark et al. |
| 5,232,925 | A | 8/1993 | Hindley |
| 5,260,445 | A | 11/1993 | Hindley |
| 5,457,109 | A | 10/1995 | Antonucci et al. |
| 5,464,856 | A | 11/1995 | Cetenko et al. |
| 5,468,762 | A | 11/1995 | Malamas et al. |
| 5,478,852 | A | 12/1995 | Olefsky et al. |
| 5,480,896 | A | 1/1996 | Malamas et al. |
| 5,494,927 | A | 2/1996 | Cetenko et al. |
| 5,496,621 | A | 3/1996 | Makita et al. |
| 5,498,621 | A | 3/1996 | Dow et al. |
| 5,510,360 | A | 4/1996 | Malamas et al. |
| 5,521,201 | A | 5/1996 | Hindley et al. |
| 5,521,202 | A | 5/1996 | Yano et al. |
| 5,523,314 | A | 6/1996 | Bue-Valleskey et al. |
| 5,814,647 | A | 9/1998 | Urban et al. |
| 6,200,998 | B1 | 3/2001 | Sahoo et al. |
| 6,646,008 | B1 | 11/2003 | Evans et al. |
| 2006/0111365 | A1 | 5/2006 | Tauchi |

FOREIGN PATENT DOCUMENTS

| | | |
|---|---|---|
| EP | 0155845 A1 | 9/1985 |
| EP | 0177353 A2 | 4/1986 |
| EP | 0193256 A1 | 9/1986 |
| EP | 0207581 A2 | 1/1987 |
| EP | 0208420 A1 | 1/1987 |
| WO | 89/08651 A1 | 9/1989 |
| WO | 91/07107 A1 | 5/1991 |
| WO | 92/02520 A1 | 2/1992 |
| WO | 94/01433 A1 | 1/1994 |
| WO | 95/18533 A1 | 7/1995 |
| WO | 95/35108 A1 | 12/1995 |
| WO | 98/25598 A2 | 6/1998 |
| WO | 01/16122 A1 | 3/2001 |
| WO | 01/16123 A1 | 3/2001 |
| WO | 2006111365 A1 | 10/2006 |
| WO | 2008/029827 A1 | 3/2008 |

OTHER PUBLICATIONS

Copland, M., et al. Dasatinib (BMS-354825) targets an earlier progenitor population than imatinib in primary CML but does not eliminate the quiescent fraction. Blood 107, 4532-4539 (2006).
Corbin, A. S., et al. Human chronic myeloid leukemia stem cells are insensitive to imatinib despite inhibition of BCR-ABL activity. J Clin Invest 121, 396-409 (2011).
De Lavallade, Hugues et al., "Imatinib for Newly Diagnosed Patients With Chronic Myeloid Leukemia: Incidence of Sustained Responses in an Intention-to-Treat Analysis," Journal of Clinical Oncology, vol. 26(20):3358-3363 (2008).
Druker et al, "Five-Year Follow-up of Patients Receiving Imatinib for Chronic Myeloid Leukemia," N. Engl. J. Med., 2006, 355, 2408-2417.
Gieske, I. et al., "Deutsches Leukamie-Studienregister 1 German Leukemia Trial Registry", Kompetenznetz"Akute und chronische Leukamien" Studiendatenbank, Jan. 1, 2010, XP055106117.
Gough, D. J., et al. Mitochondrial STAT3 supports Ras-dependent oncogenic transformation. Science 324, 1713-1716 (2009).
Graham, S. M., et al. Primitive, quiescent, Philadelphia-positive stem cells from patients with chronic myeloid leukemia are insensitive to STI571 in vitro. Blood 99, 319-325 (2002).
Gu, Chunhong et al., "Synergistic effects of troglitazone in combination with cytotoxic agents in acute myelogenous leukaemia cells," Leukemia Research, vol. 30:1447-1451 (2006).
Hiwase, et al. "Paper: Blocking of Cytokine Survival Signals along with Intense Bcr-Abl Kinase Inhibition May Eradicate CML Progenitor Cells", 51st ASH Annual Meeting and Exposition, Dec. 3, 2009, XP0551 06056.

Hoelbl, A., et al. Clarifying the role of Stat5 in lymphoid development and Abelson-induced transformation. Blood 107, 4898-4906 (2006).
Hoelbl, A., et al. Stat5 is indispensable for the maintenance of bcr/abl-positive leukaemia. EMBO Mol Med 2, 98-110 (2010).
Holyoake, T., Jiang, X., Drummond, M., Eaves, A., Eaves, C. Elucidating critical mechanisms of deregulated stem cell turnover in the chronic phase of chronic myeloid leukemia. Leukemia 16, 549-558 (2002).
Ikezoe, T., et al., "Inhibition of signal transducer and activator of transcription 5 by the inhibitor of janus kinases stimulates dormant human leukemia CD34+ /CD38– cells and sensitizes them to antileukemia agents," Int J Cancer 128, 2317-2325 (2011).
Ilaria, R. L. Jr., Van Etten, R. A. P210 and P190(BCR/ABL) induce the tyrosine phosphorylation and DNA binding activity of multiple specific STAT family members. J Biol Chem 271, 31704-31710 (1996).
International Preliminary Report on Patentability, PCT/IB2013/002583, dated May 6, 2015, 12 pages.
International Search Report and Written Opinion, PCT/IB2013/002583, dated Apr. 1, 2014, 17 pages.
Laurie, C. C. et al. Detectable clonal mosaicism from birth to old age and its relationship to cancer. Nat Genet 44, 642-650 (2012).
Luo, J., Solimini, N. L., Elledge, S. J. Principles of cancer therapy: oncogene and non-oncogene addiction. Cell 136, 823-837 (2009).
Mahon, F. X., et al. Discontinuation of imatinib in patients with chronic myeloid leukaemia who have maintained complete molecular remission for at least 2 years: the prospective, multicentre Stop Imatinib (STIM) trial. Lancet Oncol 11, 1029-1035 (2010).
Nelson, E., et al. The STAT5 inhibitor pimozide decreases survival of chronic myelogenous leukemia cells resistant to kinase inhibitors. Blood 117, 3421-3429 (2011).
Nguyen T. et al., "HDAC Inhibitors Potentiate the Activity of the BCR/ABL Kinase Inhibitor KW-2449 in Imatinib-Sensitive or -Resistant BCR/ABL+ Leukemia Cells In Vitro and In Vivo", Clinical Cancer Research, vol. 17, No. 10, Apr. 7, 2011, pp. 3219-3232, XP0551 06303.
Nguyen, L. V., Vanner, R., Dirks, P., Eaves, C. J. Cancer stem cells: an evolving concept. Nat Rev Cancer 12, 133-143 (2012).
Nieborowska-Skorska, M., et al. Signal transducer and activator of transcription (STAT)5 activation by BCR/ABL is dependent on intact Src homology (SH)3 and SH2 domains of BCR/ABL and is required for leukemogenesis. J Exp Med 189, 1229-1242 (1999).
Nievergall, E. et al., "Paper: Antibody-Targeting of IL-3 Receptor-[alpha] Increases the Susceptibility of CD34+ CML Progenitors to Dasatinib-Induced Cell Death", 53rd Annual Meeting and Exposition of the American-Society-of Hematology (ASH); San Diego, CA, USA; Dec. 10-13, 2011, Dec. 12, 2011, XP0551 06297.
O'Brien et al., "Imatinib Compared with Interferon and Low-Dose Cytarabine for Newly Diagnosed Chronic-Phase Chronic Myeloid Leukemia," N. Engl. J. Med., 2003, 348, 994-1004.
Park, Joo-In et al., "Cotreatment with Pioglitazone, a Synthetic Ligand for Peroxisome Proliferator-Activated Receptor gamma (PPARgamma), Enhances Tumor Necrosis Factor-Related Apoptosis-Inducing Ligand (TRAIL)-Induced Apoptosis of Human Leukemia Cells," Blood, ASH Annual Meeting, vol. 104, Abstract No. 4377 (2004).
Prost, S. et al., "Nef and PPAR-[gamma] interact to suppress StatS expression in CD34 progenitors from infected macaques", Medecine/Sciences 200805 FR, vol. 24, No. 5, May 2008, pp. 551-553, XP55106519.
Prost, S., et al. Human and simian immunodeficiency viruses deregulate early hematopoiesis through a Nef/PPARgamma/STAT5 signaling pathway in macaques. J Clin Invest 118, 1765-1775 (2008).
Redaelli, S., et al., "Synergistic activity of the Src/Abl inhibitor bosutinib in combination with imatinib", Leukemia, vol. 24, No. 6,Jun. 1, 2010, pp. 1223-1227, XP055106247.
Rousselot et al., Blood, Jan. 1, 2007;109(1):58-60. Epub Sep. 14, 2006.

(56) References Cited

OTHER PUBLICATIONS

Rousselot, "Targeting STAT5 Expression Resulted in Molecular Response Improvement in Patients with Chronic PhaseCML Treated with Imatinib", Abstracts and notes on CML presentations1 ASH 2012 Atlanta, Dec. 11, 2012, XP-002721324.

Rousselot, Philippe, "A phase II study to assess efficacy and safety of pioglitazone (Actos) as add-on therapy to imatinib mesylate (Gleevec) in chronic phase chronic myelogenous leukaemia (CP-CML) patients in major molecular responses," retrieved online at: http://www.kompetenznetz-leukaemia.de/trial/en/detail_trial.html?id=337, 2 pages, (2010).

Sohda, T et al., Studies on Antidiabetic Agents. II. 1) Synthesis of 5-[4-(1-Methylcyclohexylmethoxy)-benzyl]thiazolidine-2,4-dione (ADD-3878) and its Derivatives) Chem. Pharm, Bull 30 (10) 3580-3600, (1982).

Walz, C., et al. Essential role for Stat5a/b in myeloproliferative neoplasms induced by BCR-ABL1 and JAK2(V617F) in mice. Blood 119, 3550-3560 (2012).

Wang, L., Giannoudis, A., Austin, G., Clark, R. E. Peroxisome proliferator-activated receptor activation increases imatinib uptake and killing of chronic myeloid leukemia cells. Exp Hematol 40, 811-819 (2012).

Wang, Z., Li, G., Tse, W., Bunting, K. D. Conditional deletion of STAT5 in adult mouse hematopoietic stem cells causes loss of quiescence and permits efficient nonablative stem cell replacement. Blood 113, 4856-4865 (2009).

Warsch, W., et al. High STAT5 levels mediate imatinib resistance and indicate disease progression in chronic myeloid leukemia. Blood 117, 3409-3420 (2011).

Zhou, J. et al., "Synergistic antileukemic effects between ABT-869 and chemotherapy involve downregulation of cell cycle-regulated genes and cMos-mediated MAPK pathway",Leukemia, vol. 22, No. 1, Jan. 1, 2008, pp. 138-146, XP055106229.

* cited by examiner

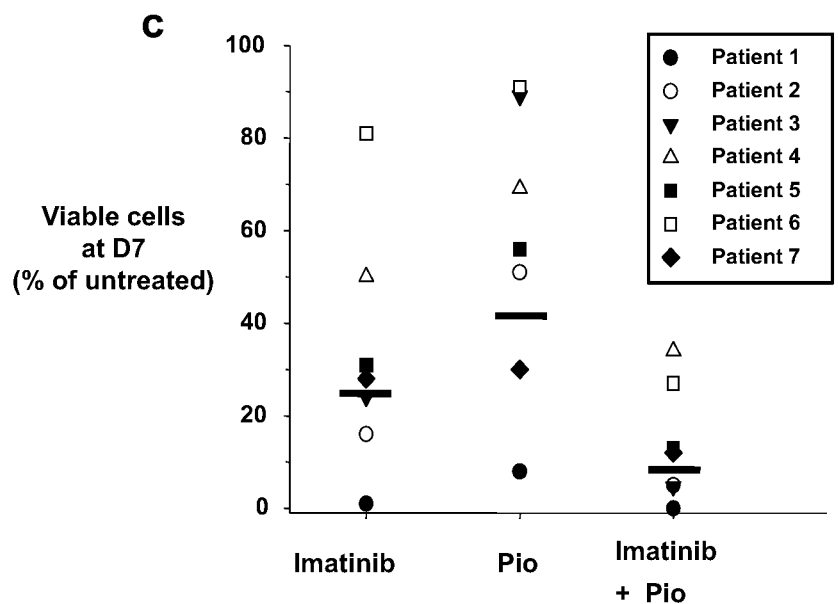
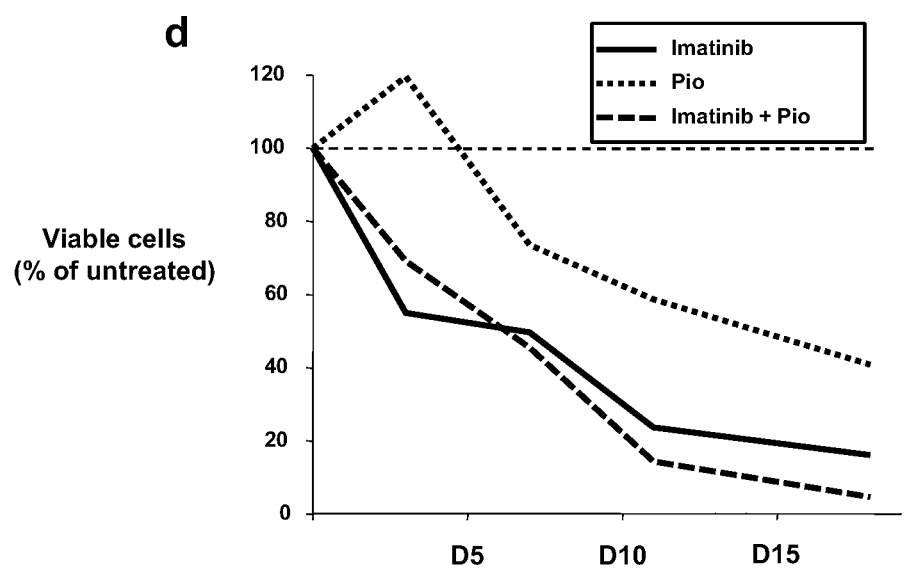
Fig. 1- cont.

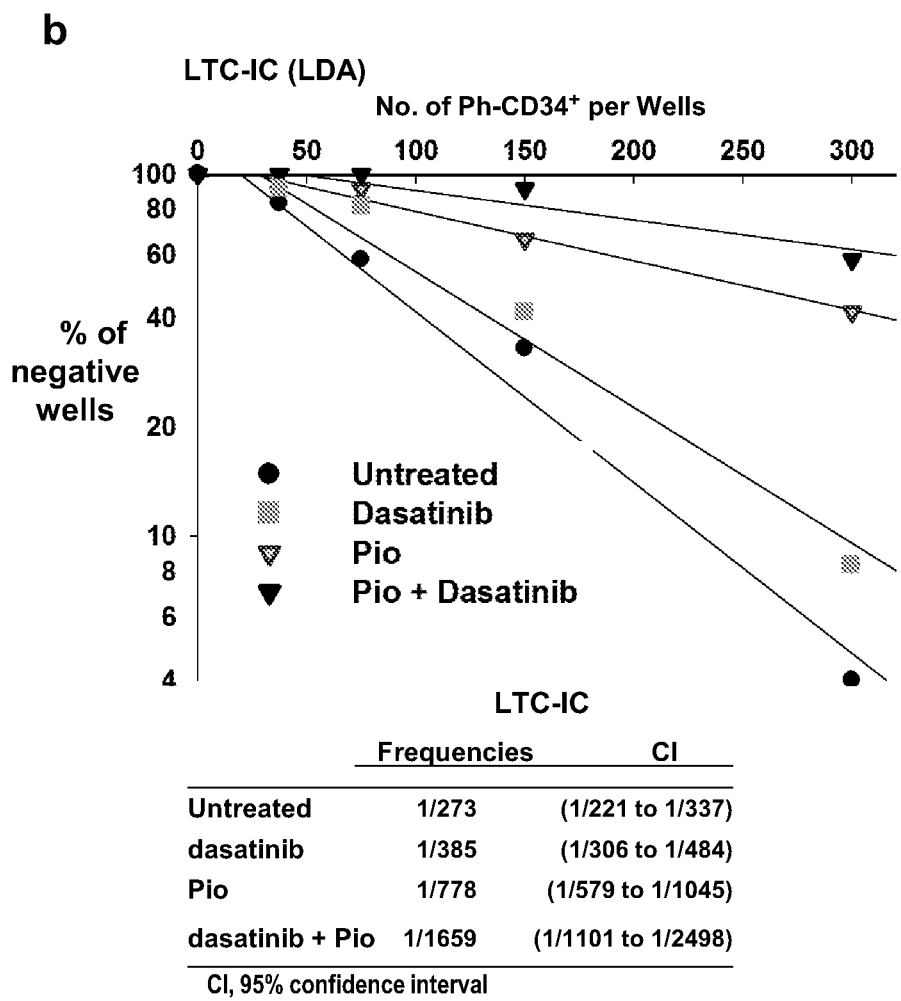
Fig. 2-cont.

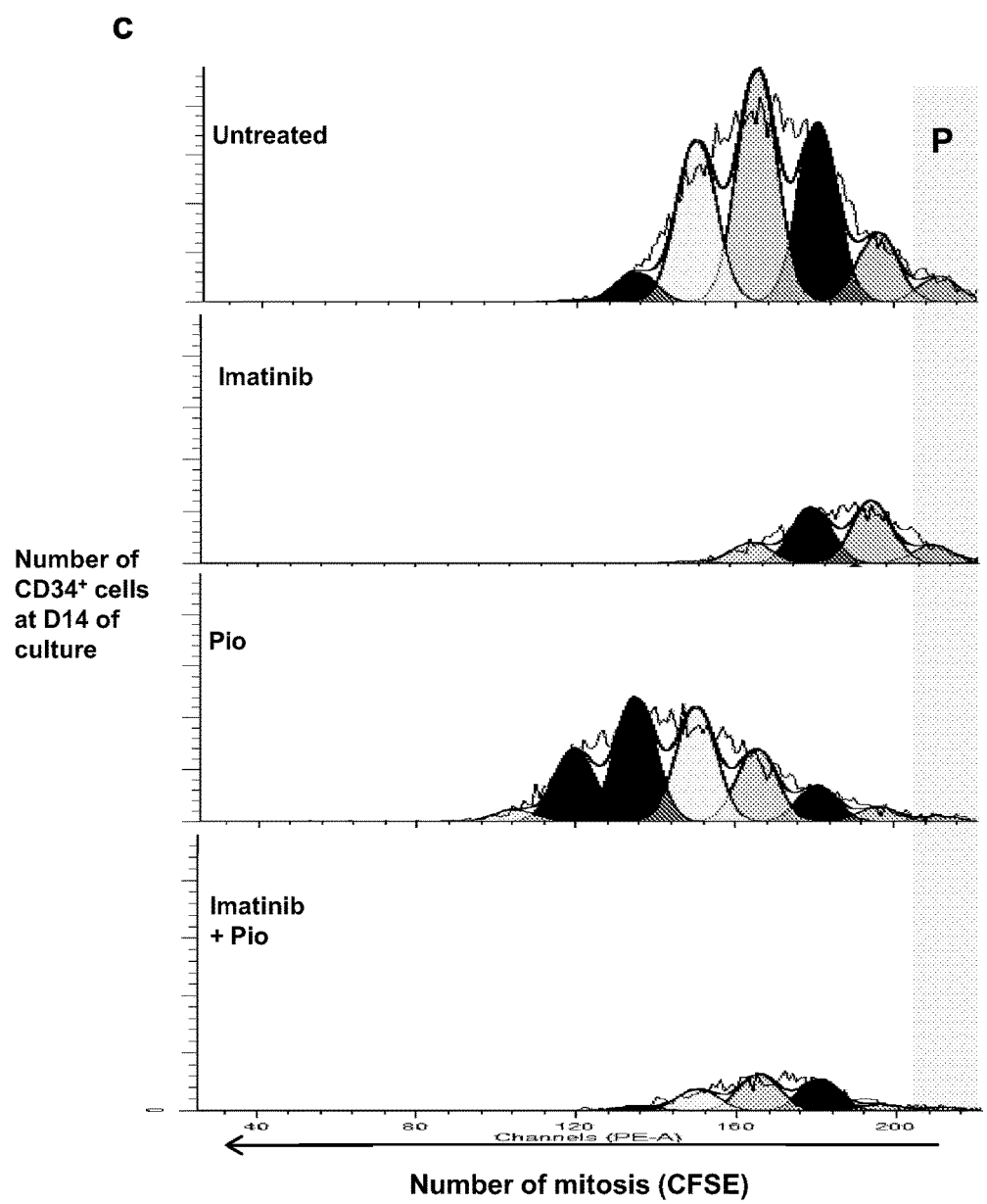
Fig. 2-cont.

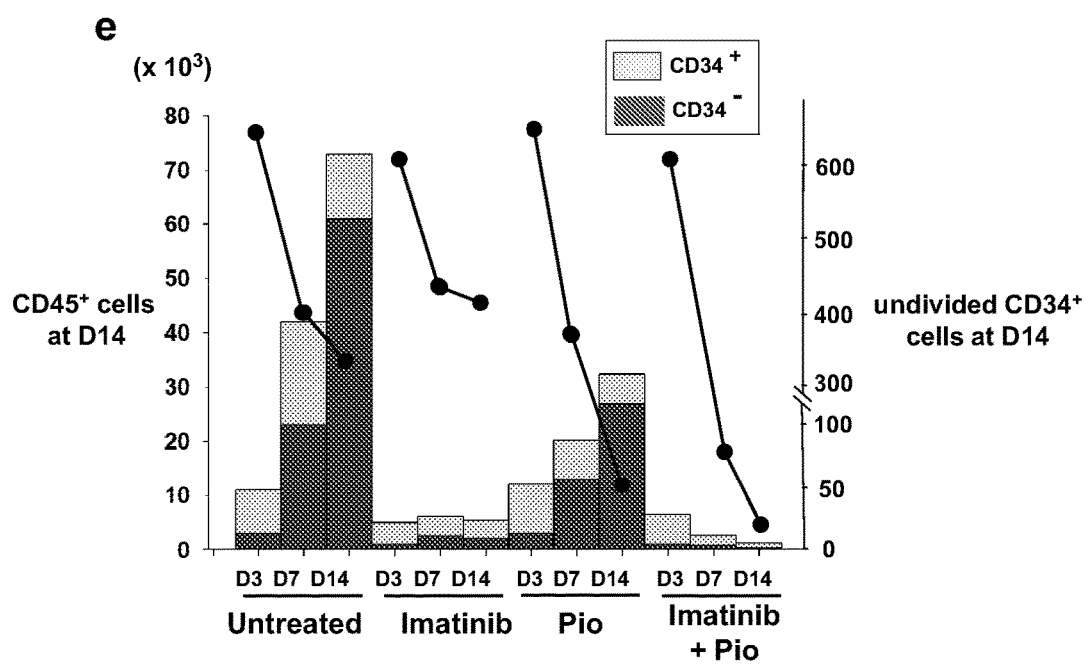
Fig. 2-cont.

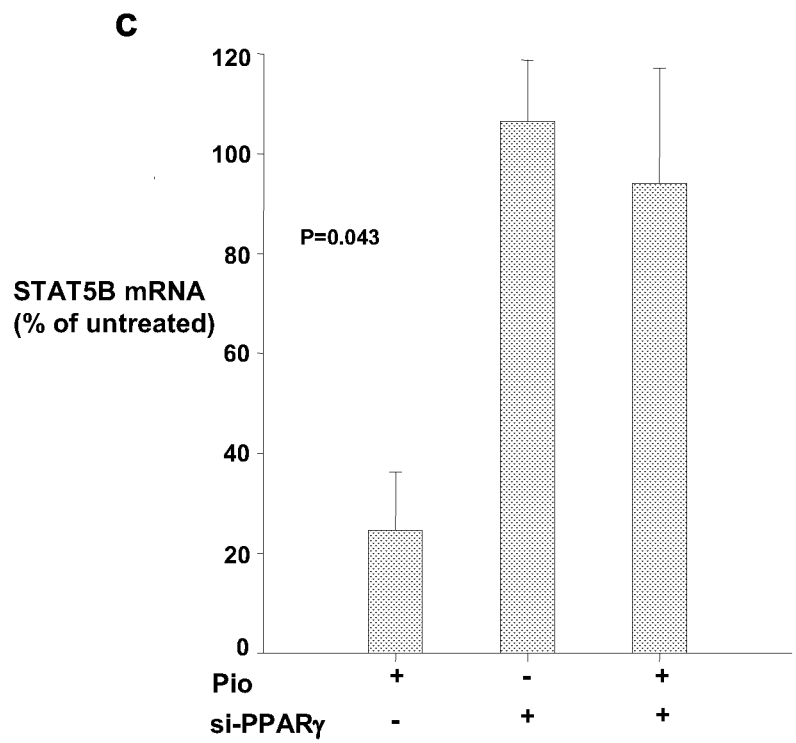
Fig. 3- cont.

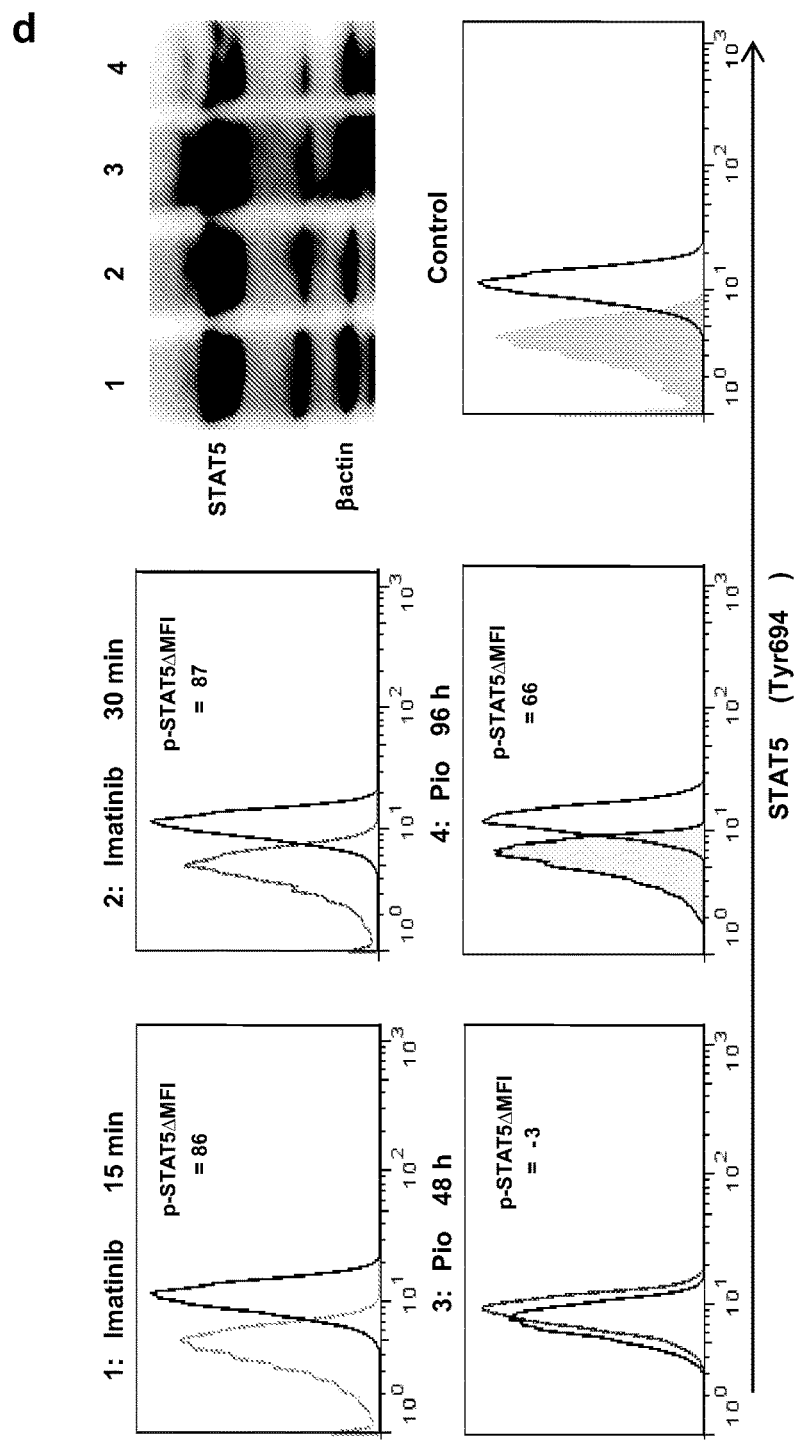
Fig. 3- cont.

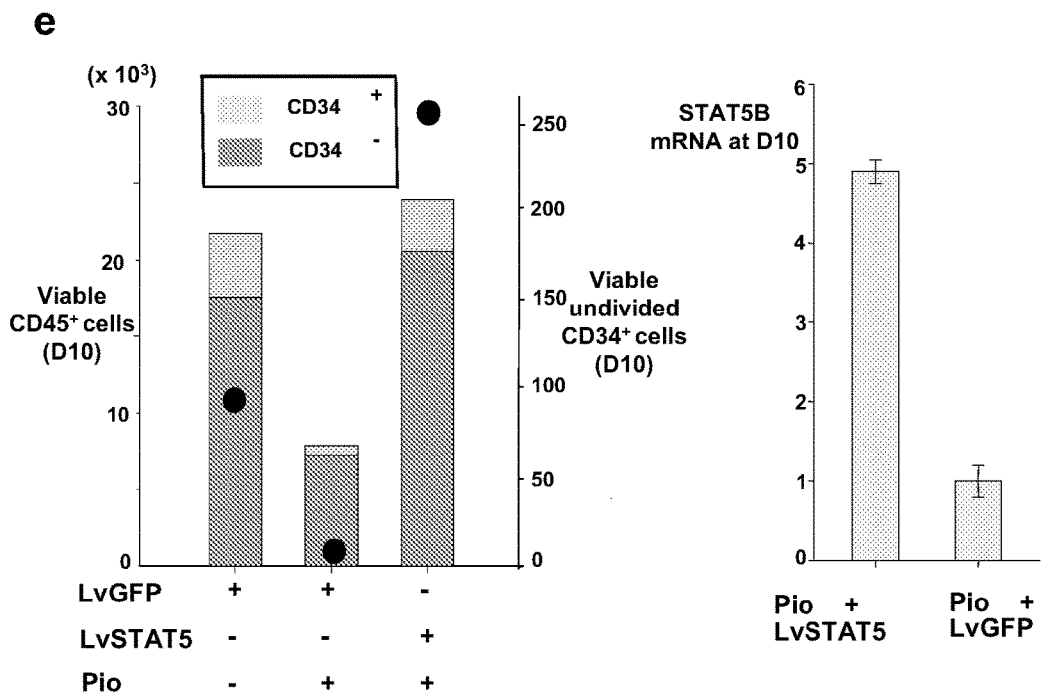
Fig. 3- cont.

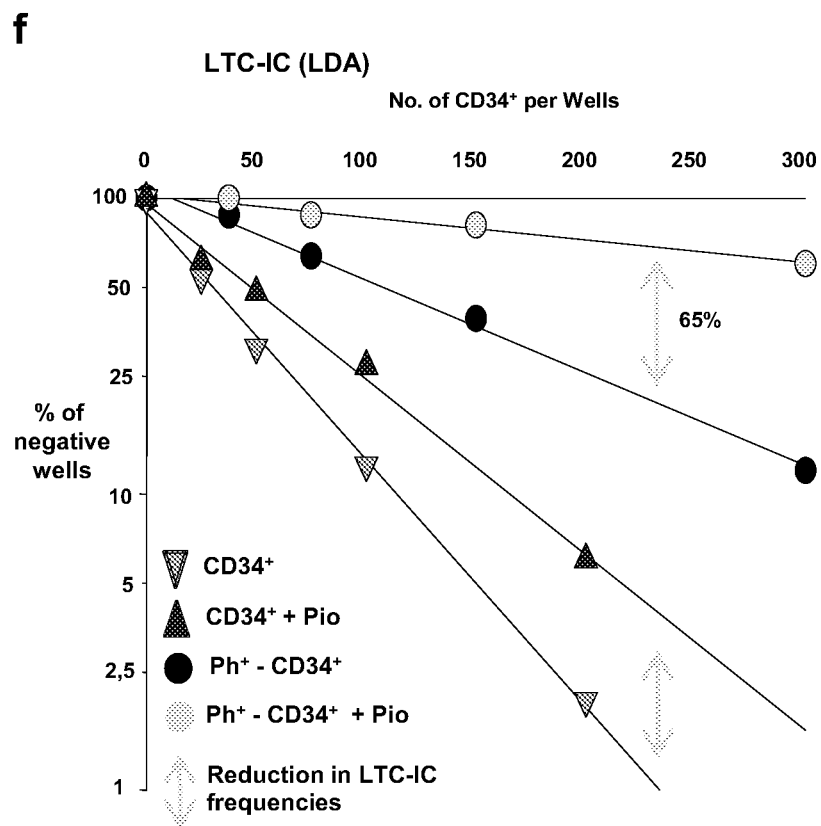
Fig. 3- cont.

COMBINATION OF AN ANTI-CANCER AGENT SUCH AS A TYROSINEKINASE INHIBITOR AND A STAT5 ANTAGONIST, PREFERABLY A THIAZOLIDINEDIONE, FOR ELIMINATING HEMATOLOGIC CANCER STEM CELLS IN VIVO AND FOR PREVENTING HEMATOLOGIC CANCER RELAPSE

RELATED APPLICATIONS

This application is a 35 U.S.C. §371 national stage application of International Patent Application No. PCT/IB2013/002583, filed on Nov. 5, 2013, which claims priority to and benefit of U.S. Provisional Application Nos. 61/722,633 filed Nov. 5, 2012 and 61/794,367 filed Mar. 15, 2013, the contents of each of which are hereby incorporated by reference herein.

BACKGROUND

Bone marrow-hematopoietic stem cells (HSCs) are functionally defined by their unique capacity to self-renew and to differentiate to produce all mature blood cell types. In general, the process of development from pluripotent progenitors to mature cells with specific functions involves the progressive loss of developmental potential to other lineages. This process has been considered linear in the sense that once a cell has made a developmental choice it cannot revert. The earliest known lymphoid-restricted cell in adult mouse bone marrow is the common lymphocyte progenitor (CLP) and the earliest known myeloid-restricted cell in adult mouse bone marrow is the common myeloid progenitor (CMP), CD34$^+$ cells harbor virtually all in vitro clonogenic potential; however, the CD34$^+$ population is heterogeneous. Only a small fraction (1-10%) of CD34' cells that do not express mature lineage markers (CD3, CD4, CD8, CD19, CD20, CD56, CD11b, CD14 and CD15; Lin−) have multi lineage (lymphoid and myeloid) developmental potential. The majority of CD34$^+$ cells (90-99%) co-express the CD38 antigen, and this subset contains most of the lineage-restricted progenitors. Deregulation of self-renewal pathways, which are normally tightly regulated in HSCs, has recently been recognized as an important step in leukemic progression.

Myeloid (myelogenous or non-lymphocytic) hemopathies include acute myeloid leukemia (AML) and chronic hemopathies named as myeloproliferative myelodysplasic diseases (MPDs or CMPs). Acute leukemia is characterized by the rapid increase of immature blood cells and can occur in children (ALL) and young adults (AML). Myeloproliferative diseases (MPDs) are a heterogenous group of chronic clonal disorders characterized by cellular proliferation of one or more hematologic cell lines in the peripheral blood, distinct from acute leukemia. Proliferation takes months to years to progress and is distinguished by the excessive build up of relatively mature abnormal blood cells; resulting in increased numbers of granulocytes, red blood cells and/or platelets in the peripheral blood. Myeloproliferative diseases include: Chronic myelogenous leukemia (CML), Polycythemia vera (PV), Essential thrombocythemia (ET), Chronic idiopathic myelofibrosis (Agnogenic myeloid metaplasia (AIM)), Chronic neutrophilic leukemia (CNL), Chronic eosinophilic leukemia/hypereosinophilic syndrome (CEL/HES) and systemic mastocytosis (SM). Myeloproliferative disease may evolve into one of the other myeloproliferative conditions, transform to acute leukemia, or both.

With the exception of chronic myeloid leukemia (CML), the molecular pathogenesis of most chronic myeloproliferative disorders (CMPDs) is not well understood and most CMPD cases have a normal or aneuploid karyotype. However, CML, and some CMPDs are associated with activation of membrane or cytoplasmic Protein Tyrosine Kinases (PTK) by point mutation or chromosomic translocation of respectively the KIT, FLT3 and JAK2 genes or the ABL, PDGFR, 15 FGFRI and FGFR3 genes. Chronic myelogenous leukemia is characterized by t(9;22)(q34;q11) reciprocal translocation (der22 or Ph+ chromosome) and BCR-ABL fusion protein expression. The dysregulated cytoplasmic tyrosine kinase activity of BCR-ABL is responsible for the leukemic phenotype. The BCR-ABL protein is referred to as p185$^{bcr-abl}$ or p210$^{bcr-abl}$, depending upon the inclusion of the second exon of BCR. p185$^{bcr-abl}$ causes acute leukemia, typically lymphoblastic; p210$^{bcr-abl}$ usually causes CML which may progress to myeloid or lymphoid blast crisis. In polycythemia vera, essential thrombocythemia, and myelofibrosis, the prevalent genetic lesion appears to be a valine to phenylalanine substitution at amino acid position 617 (V617F) within the Janus kinase 2 (JAK2) gene. AML and systemic mastocytosis have been linked with the D816 mutation of the KIT gene. The BCR-PDGFRα or F1P1L1-PDGFRα fusions have been identified in patients with hypereosinophilic syndrome.

Imatinib, a 2-phenylaminopyrimidine molecule, occupies the ATP binding site and inhibits tyrosine phosphorylation of ABL, c-KIT and PDGFRα. Imatinib mesylate (STI571, Gleevec or Glivec) was the first tyrosine kinase inhibitor (TKI) targeted against BCR-ABL to be successfully tested in vivo and is now the gold standard for the treatment of de novo CML in chronic phase (O'Brien et al., N. Engl. J. Med., 2003, 348, 994-1004; Druker et al, N. Engl. J. Med., 2006, 355, 2408-2417). The remarkable efficacy of imatinib has failed, however, to eradicate this disorder, and residual CML disease remains detectable by PCR for most of the patients. Even in patients with complete molecular remission (CMR) for more than two years, molecular relapses within 6 months are observed in half of the patients (Rousselot et al., Blood, 2007 Jan. 1; 109(1):58-60. Epub 2006 Sep. 14).

Imatinib inhibits the tyrosine kinase activity of BCR-ABL and eradicates the proliferating pool of CML cells without being active on CML quiescent cells.

Recent studies have identified a population of rare primitive, quiescent stem cells (LSCs) in all CML patients, whether derived from peripheral blood or blood marrow. These stem cells are predominantly Ph+, express high levels of CD34$^+$ but lack the markers CD38, CD45RA or CD71, and can spontaneously exit $G_o$ to enter a continuously proliferating state, to produce Ph+ progeny (Graham et al., Blood, 2002, 99, 319-325; Barnes et al., Cell cycle, 2006, 5, 2862-2866). These cells exhibit an exceptionally high level of inherent insensitivity to conventional chemotherapeutic agents, including imatinib mesylate. Such insensitivity is distinct from acquired resistance, following chronically exposition to the drug whereby resistance to imatinib is frequently mediated by the selection of subclones containing BCR-ABL with point mutations in the ABL-kinase domain. Other mechanisms which have been implicated in clinical resistance (acquired resistance or secondary resistance) to imatinib include over expression of BCR-ABL, amplification of the BCR-ABL oncogene and enhanced drug efflux.

This inherent insensitivity or resistance to drug treatment has important implications for the clinical management of CML-, particularly with regard to relapse following an imatinib-induced remission. However, contrary to acquired resistance to imatinib, the molecular mechanisms responsible for the insensitivity of CML quiescent stem cells are not known. Therefore, there are no obvious molecular targets and no rational choices can be made regarding which agents to combine with imatinib to target the CML quiescent stem cells. Several approaches have been used to try to improve the effectiveness of imatinib; intermittent exposure to granulocytecolony stimulating factor (G-CSF) and vaccination with T peptides able to induce specific cytotoxic T-cell response. Accordingly, improved therapies for preventing hematological cancer relapse are needed.

SUMMARY

The present invention provides methods for reducing or eliminating hematologic cancer stem cells in vivo, and thus preventing relapse, by co-administering an anti-cancer agent (e.g., a TKI), followed by a Signal Transducer and Activator of Transcription 5 (STAT5) antagonist (e.g., a PPARγ agonist) which, in turn, downregulates HIF 2a.

In one aspect, the invention provides a method of eliminating hematologic cancer stem cells in vivo comprising: (A) administering to a patient with hematologic cancer, an effective amount of an anti-cancer agent; and (B) administering to the patient an effective amount of a Signal Transducer and Activator of Transcription 5 (STAT5) antagonist.

In another aspect, the invention provides a method of preventing hematologic cancer relapse in a patient comprising: (A) administering to the patient an effective amount of an anti-cancer agent; and (B) administering to the patient an effective amount of a STAT5 antagonist.

Each of the above aspects of the invention can include one or more of the following embodiments.

In some embodiments, the anti-cancer agent (e.g., TKI) is administered prior to the STAT5 antagonist (e.g., thiazolidinedione compound), until a stable cumulative incidence of response in the patient is achieved. In certain embodiments, the response is selected from the group consisting of complete hematological remission (CHR), major cytological remission (MCR), complete cytological remission (CCR), major molecular remission (MMR) and complete molecular remission (CMR). In various embodiments, the anti-cancer agent is administered for at least 3, 6, 9, 12, 15, 18, 21, 24, 27, 30 or 33 months or more prior to administration of the STAT5 antagonist.

In other embodiments, the STAT5 antagonist is administered (after the above initial course of treatment with the anti-cancer agent) for at least 2, 4, 6, 8, 10 or 12 months, or any range therebetween (e.g., 2-12 or 2-6 months or more), concurrently with the anti-cancer agent. Administration of the anti-cancer agent can be continued after administration of the STAT5 antagonist is terminated (whether temporarily or permanently terminated). In various embodiments, administration of the anti-cancer agent is continued for 2-12 more months or longer (even for life), as needed to sustain full remission (e.g., CMR). In other embodiments, the anti-cancer agent is discontinued permanently once a clinically complete remission is achieved in the patient.

In various embodiments, the STAT5 antagonist is a peroxisome proliferator-activated receptor gamma (PPARγ) agonist. In a particular embodiment, the STAT5 antagonist is a thiazolidinedione compound, such as a glitazone compound (e.g., pioglitazone, rosiglitazone, troglitazone, englitazone, ciglitazone or netoglitazone). In a specific embodiment, the thiazolidinedione compound is pioglitazone. STAT5 antagonists employed in the invention serve to suppress expression of the transcription factor, HIF 2a, allowing quiescent stem cells (LSCs) to proliferate, and potentiating the effect of anti-cancer therapeutics, such as TKIs.

In other various embodiments, the patient has leukemia. In particular embodiments, the patient has chronic myeloid leukemia (CML) or acute myeloid leukemia.

In further embodiments, the anti-cancer agent is a tyrosine kinase inhibitor (TKI). In particular embodiments, the TKI is selected from the group consisting of imatinib, gefitinib, erlotinib, dasatinib, nilotinib, bosutinib, ponatinib, ruxolitinib, quizartinib and sunitinib. In a specific embodiment, the TKI is imatinib.

In certain embodiments, the STAT5 antagonist is administered at a dose of about 15-60 mg/day (e.g., about 30-50 mg/day or within other range of tolerated toxicity). For example, the STAT5 antagonist can be administered at a dose of about 30 mg/day for 2 months and about 45 mg/day. In other embodiments, the anti-cancer agent is administered at a dose of about 300-800 mg/day (e.g., about 300-400 mg/day).

In a particular embodiment, the hematological cancer is a myeloid cancer (e.g., CML), the thiazolidinedione compound is pioglitazone and the TKI is imatinib. The TKI is preferably administered until a stable cumulative incidence of response is achieved in the patient, followed by administration of the pioglitazone until a complete molecular response (CMR) is achieved. In one embodiment, the TKI (e.g., imatinib) is administered at about 300-400 mg/day and the thiazolidinedione (e.g., pioglitazone) is administered at about 30-50 mg/day.

Other features and advantages of the invention will be apparent from the following detailed description and the claims.

DETAILED DESCRIPTION

Figure 1:
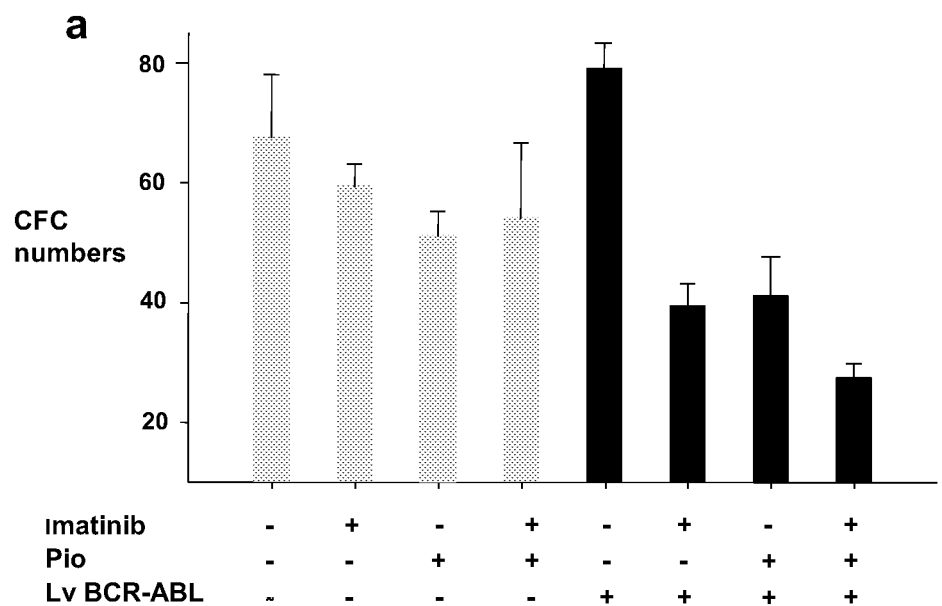
FIG. 1 (a)-(d) shows differential and synergistic effects of pioglitazone and imatinib on CML cells.
Figure 1:
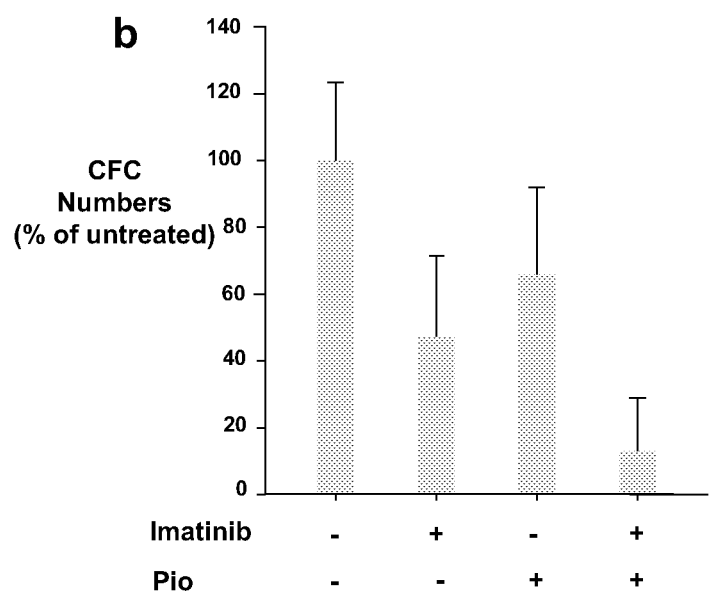

The present invention is based, in part, on the unexpected discovery that quiescent cancer stem cells (e.g., myeloid leukemia stem cells) are highly dependent on ("addicted" to) STAT5, and thus can be selectively targeted and eradicated by down regulating STAT5, particularly during or following conventional chemotherapy.

Given that quiescent stem cells often are responsible for relapse and resistant to standard chemotherapies, the invention provides an effective, targeted method for preventing cancer relapse. As demonstrated herein, administration to leukemia patients of STAT5 inhibitors (e.g., PPARγ agonists, such as glitazones), following standard chemotherapy (e.g., administration of anti-cancer agents), results in sustained, long-term remission, even at undetectable levels. Moreover, the significant dependency of quiescent stem cells on STAT5 allows for administration of the STAT5 inhibitor at levels which are tolerated by patients. Prior to the present invention, this would not have been thought possible, since it would have been believed necessary to have administered high doses of the inhibitor sufficient to eradicate the majority of stem cells in a patient, even normal stem cells which are not STAT5 addicted (in a non-selective manner).

Definitions

As used herein, "patient" refers to a human cancer patient.

As used herein, "treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, preventing, eradicating, reducing, slowing, retarding, or stabilizing of a deleterious progression of a marker of cancer. For example, treatment may refer to reducing the clonogenic activity of hematologic cancer stem cells. Treatment may also refer to inhibiting growth of BCR-ABL positive cells. Treatment may further refer to inducing a clonogenic and/or proliferative defect in hematologic cancer stem cells. Treatment may also refer to down regulating STAT5 activity in hematologic cancer stem cells. Treatment may further refer to achieving a major molecular response (MMR), complete molecular response (CMR) or a complete cytological response (CCR) in a patient having hematologic cancer.

As used herein, "hematologic cancer" refers to cancer that affects blood, bone marrow, and lymph nodes. In certain embodiments, the cancer may derive from either of the two major blood cell lineages: myeloid and lymphoid cell lines. In some embodiments, the hematologic cancer includes myeloid cancer. In various embodiments, the myeloid cancer can include chronic myeloid cancer (CML) and acute myeloid cancer (ACL).

As used herein, "stem cells" refer to Cancer stem cells (CSCs) or cancer cells found within hematological cancers that possess characteristics associated with normal stem cells For example, the ability to give rise to all cell types found in a particular cancer sample. CSCs are tumorigenic (tumor-forming) cells. In some embodiments, CSCs can generate tumors through the stem cell processes of self-renewal and differentiation into multiple cell types. In certain embodiments, such cells can persist in tumors as a distinct population and cause relapse and metastasis by giving rise to new tumors.

Figure 7:
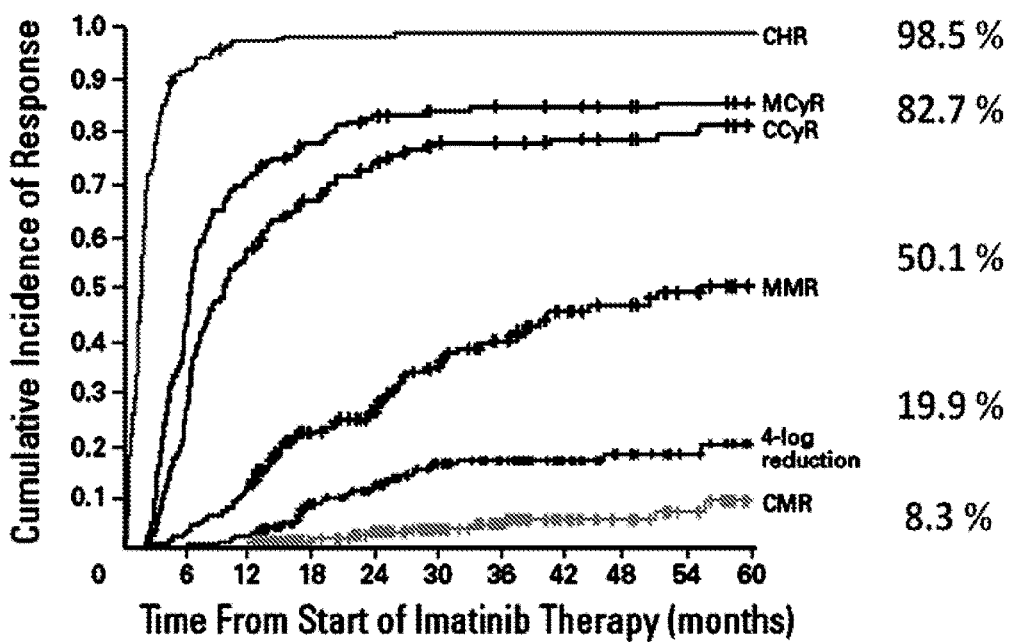
FIG. 7 shows the cumulative incidence of response (CIR) following treatment with 400 mg/day of oral imatinib.
Figure 8:
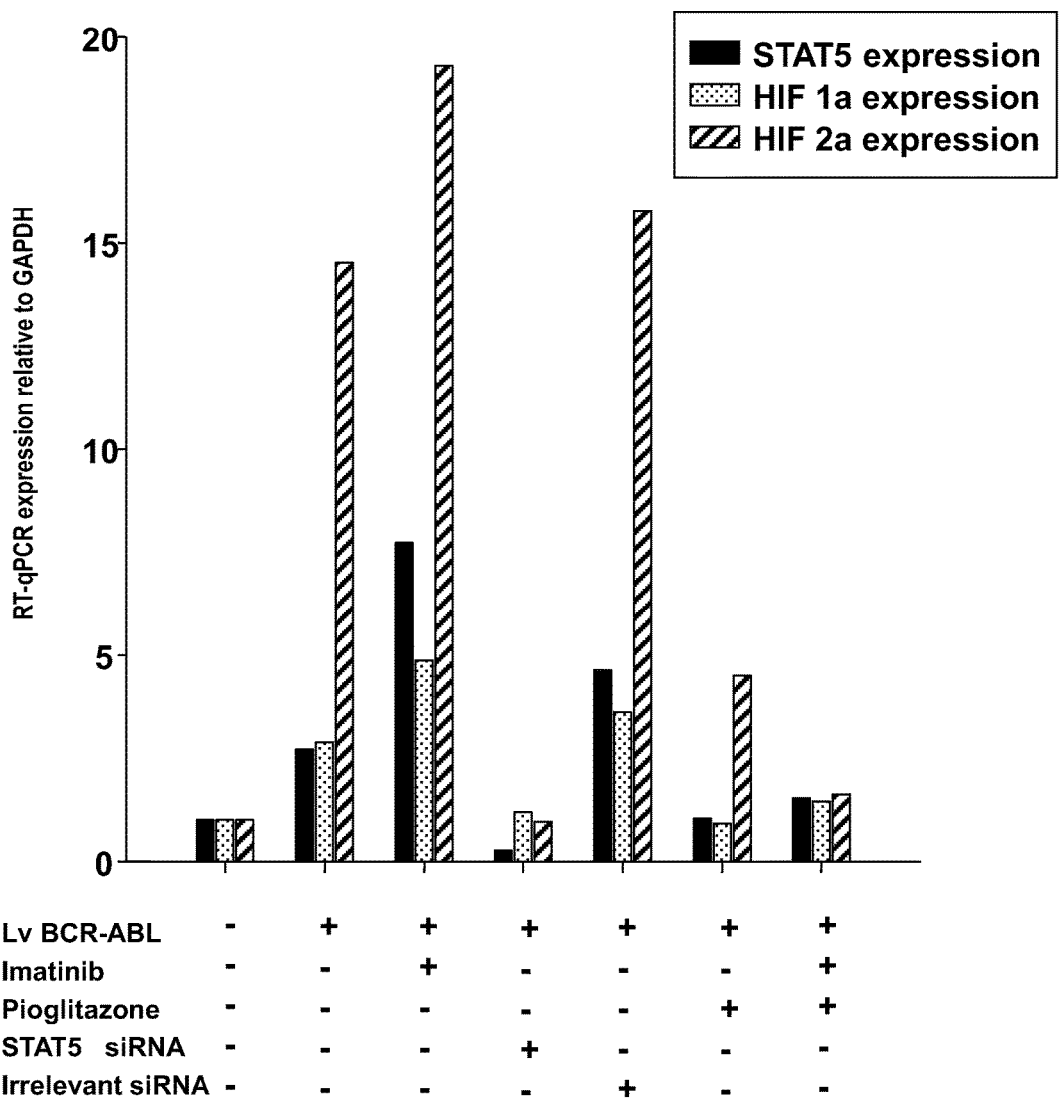
FIG. 8 shows the specificity of STAT5 antagonist action in BCR-ABL expressing (CD34+) cells on HIF 1a and HIF 2a expression.

As used herein, "effective amount" refers to an amount of one or more agents that results in a stable cumulative incidence of response in a patient. A stable cumulative incidence of response can be achieved, for example, in the form of a stable complete hematological remission (CHR), major cytological remission (MCR) or (MCyR), complete cytological remission (CCR) or (CCyR), major molecular remission (MMR) or complete molecular remission (CMR) in a patient having hematologic cancer. In a particular embodiment, a stable cumulative incidence of response with respect to MCR or CCR is achieved when values of the Philadelphia chromosome (Ph-positive) metaphases measured in multiple consecutive bone marrow examinations over a period of 6 months do not vary more than 20%. In another embodiment, a stable cumulative incidence of response with respect to MMR or CMR is achieved when the BCR-ABL transcript levels measured, for example using quantitative real-time PCR, in multiple consecutive examinations over a period of 6 months do not vary more than 20%. FIG. 7 depicts the cumulative incidence of response (CIR) following treatment with 400 mg/day of oral imatinib. A stable cumulative incidence of response is achieved for example when each curve representing CHR, MCR, CCR, MMR and CMR respectively, reaches a plateau, i.e., when the difference in the cumulative incidence of response over a period of 6 months is ≤0.2.

As used herein "complete hematological remission (CHR)" refers to achieving a stage when the blood counts of the patient have returned to normal levels, i.e., the levels usually observed in a healthy person.

As used herein, "major cytological remission (MCR) or (MCyR)" refers to achieving a stage when a combined number of cytological responses corresponds to ≤35% Philadelphia chromosome (Ph-positive) metaphases.

As used herein, "complete cytological remission (CCR) or (CCyR)" refers to achieving a stage of failure to detect any Philadelphia chromosome (Ph-positive) metaphases in two consecutive bone marrow examinations with a minimum of 30 metaphases examined. In some embodiments, CCR refers to the absence of cancer cells of the myeloid lineages (blasts) in the blood and blood marrow of a subject previously having a myeloid hemopathy associated with STAT5 activation that was treated with an anti-cancer agent. The cytological response is assayed by methods known in the art including: Light microscopy morphologic detection, clonogenic assays, immunophenotype analysis, karyotype analysis, Fluorescence and In Situ Hybridization.

As used herein, "major molecular remission (MMR)" refers to achieving a significant decrease in the number of BCR-ABL transcripts. In some embodiments, MMR is achieved when a 10 fold decrease in the number of BCR-ABL transcripts is detected. In certain embodiments MMR is achieved when a 3-log reduction in transcript levels on the basis of two consecutive molecular studies is observed.

As used herein, "complete molecular remission (CMR)" refers to a decrease in the number of BCR-ABL transcripts such that it is virtually undetectable. In some embodiments, CMR is achieved when a 1000 fold decrease in the number of BCR-ABL transcripts is detected. In various embodiments, CMR is achieved when two consecutive samples result in no detectable transcripts.

CMR also refers to the absence of cells of the myeloid lineage that express a molecular marker of the myeloid hemopathy in the blood and blood marrow of a patient previously having a myeloid hemopathy associated with STAT5 activation that was treated with an anti-cancer agent. The molecular marker can be the mutated tyrosine kinase responsible for the myeloid hemopathy, which is detected by methods known in the art, for example by RT-QPCR. Usually a marker specific for the cancer cells and a marker specific for the normal cells of the same type are detected simultaneously to determine the efficiency of. treatment.

As used herein, "clinically complete remission" refers to achieving an undetectable level of BCR-ABL transcript for an extended period of time. In some embodiments, clinically complete remission refers to a one year cumulative incidence of CMR4.5. CMR4.5 is defined by a BCR-ABL/ABL IS ratio ≤0.0032%. In certain embodiments, clinically complete remission refers to achieving a sustained CMR up to 4.5 years after withdrawal of the STAT5 antagonist as well as the anti-cancer agent.

As used herein, "agent" refers to a chemical, compound, a mixture of chemical compounds, a biological macromolecule, or an extract made from biological materials such as bacteria, plants, fungi, or animal (particularly mammalian) cells or tissues.

As used herein, "anti-cancer agent" refers to any agent that has the functional property of inhibiting the proliferation of hematopoietic cells of the myeloid lineage and of inhibiting the development or progression of a myeloid hernopathy, except STAT5 antagonists and PPARγ agonists. Anti-cancer agent includes with no limitation; mitotic inhibitors, such as vinblastine; alkylating agents, such as cisplatin, carboplatin and cyclophosphamide; antimetabolites, such as 5-fluorouracil, cytosine arabinoside, hydroxyurea; nucleic acid intercalating agents, such as adriamycin and bleomycin; enzymes, such as asparaginase; topoisomerase inhibitors, such as etoposide; biological response modifiers, such as interferon; apoptotic agents, such as actinomycin D; antihormones, for example antioestrogens such as tamoxifen or, for example antiandrogens; agents which increase immune response to tumors and signal transduction inhibitors. Other examples of anti-cancer agents include: heat shock protein inhibitors (17-AAG), farnesyltransferase inhibitors (zarnestra), histone deacetylase inhibitors (SAHA, depsipeptide, MS-275.), CDK inhibitors (flavopiridol), proteasome inhibitors (bortezomib), demethylating agents (decitabine, vizada), Bcl-2 inhibitors (ABT-737), anthracyclines, daunorubicin, doxorubicin, idarubicin, cytarabine, etoposide, dexamethasone, methotrexate, thioguanine, 6-mercaptopurine, ATRA, gemcitabine, vincristine, prednisone, mitoxantrone, and rituxan.

As used herein "TKI" refers to a tyrosine kinase inhibitor, i.e., an agent that can inhibit the function of the enzyme tyrosine kinase.

In some embodiments, the anti-cancer agent is a tyrosine kinase inhibitor. Examples of tyrosine kinase inhibitors include: Imatinib, AMN107, Dasitinib (BMS-354825), nilotinibb (Tasigna®, NOVARTIS), CHIR-258, CEP-701, PKC412, SU11248, SU5416, SU5402, PD173074 and MLN518. Preferably, the tyrosine kinase inhibitor inhibits BCR-ABL phosphorylation. More preferably, the tyrosine kinase inhibitor is selected from the group consisting of: Imatinib, AMN107, Dasitinib (BMS-354825) and nilotinib (Tasigna®, NOVARTIS).

In some embodiments, the TKI is imatinib. In certain embodiments, the TKI is dasatinib. In various embodiments, the TKI is nilotinib. In some embodiments, the TKI is bosutinib. In certain embodiments, the TKI is ponatinib. In various embodiments, the TKI is ruxolitinib. In some embodiments, the TKI is quizartinib.

As used herein, "STAT5 antagonist" refers to any agent which inhibits expression and/or activity of STAT5 which, in turn, regulates HIF 2a expression. Such agents include, for example, siRNA, shRNA and known small molecule compounds. In some embodiments, a STAT5 antagonist is a PPARγ agonist.

As used herein, "PPARγ" refers to members of the peroxisome proliferator-activated receptors family which are expressed, inter alia, in adipocytic and hematopoietic cells (Braissant, O. et al. Endocrinology 137(1): 354-66), and which function as key regulators of differentiation. Contemplated within this definition are variants thereof, as for example, PPARγ1 and PPARγ2 which are two isoforms having a different N terminals generated by alternate splicing of a primary RNA transcript (Tontonoz, P, et al., Genes & Dev., 1994, 8:1224-34; Zhu et al., J, Biol. Chem., 1993, 268: 26817-20).

As used herein, "PPARγ agonist" refers to an agent which mimics a natural ligand to the PPARγ receptor and inhibits STAT5 transcription in a hematopoietic cell. It includes any naturally-occurring or non-naturally occurring agents that selectively and specifically bind to a PPARγ protein and upon binding, activate transcription of genes which contain a PPARγ responsive element. Examples of such ligands include, but are not limited to thiazolidinedione and derivatives thereof, or prostaglandin (PG) metabolites, e.g., prostaglandin 15-deoxy-A2' 14, PGD2, and derivatives thereof.

Compounds useful for practicing the present invention and methods of making these compounds are known. Examples of PPARγ agonists are disclosed in International PCT applications WO 91/07107; WO 92/02520; WO 94/01433; WO 89/08651; WO 30 95/18533; WO 95/35108; WO 98/25598; WO 01/16122; WO 01/16123; Japanese patent publication 69383/92; and U.S. Pat. Nos. 5,523,314; 5,521,202; 5,510,360; 5,498,621; 5,496,621; 5,494,927; 5,480,896; 5,478,852; 5,468,762; 5,464,856; 5,457,109; 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5 5,232,925; 5,260,445; 5,814,647 and 6,200,998.

In certain embodiments, the STAT5 antagonist, e.g., PPARγ agonist is a thiazolidinedione compound. The thiazolidinedione compound that is used in the combined preparation of the invention can be selected from:

5-[442-(5-ethylpyridin-2-yl)ethoxylThenzylithiadiazoli-dine-2,4-dione or 5-44-(2-(5-ethyl-2-pyridinyl)ethoxy) phenyOmethyl)-2,4-thiazolidinedione pioglita.zone (Actose or Glutin® TAKEDA);

544-[(1-methylcyclohexyl)methoxy]benzylithiadiazoli-cline-2,4-dione; ciglitazone;

5-[(2-benzyl-2,3-dihydrobenzopyran)-5-yhnethyl]thiadi-azoline-2,4dione: englitazone;

54[41-[(3,4-dihydro-6-hydroxy-2,5,7,8-tetramethyl-2H-1-benzopyran-2-yOmethoxy]phenylimethyll-2,4-thiazoli-dinedione or 5-(44(6-hydroxy-2,5,7,8-tetramethylchro-man-2-yl-methoxy)benzyl)-2,4-thiazoliclittedione troglitazone (Rezulin®, Resulin® or Romozine);

54[4-2-(methyl-2-pyridinylamino)ethoxy]phenyljmethyl12, 4-thiazolidineclione rosiglitazone (Avandia®; GLAXOS-MITHKLINE) 5-[(2-alkoxy-5-pyridyl)methyl]-2,4-thi-azolidinedione;

5-[(substituted-3-pyridyl)methyl]-2,4-thiazolidinedione;

544-(2-methyl-2-phenylpropoxy)benzyllthiazolidine-2,4-dione;

54443-(4-methoxyphenyl)-2-oxooxazolidin-5-yli-methoxyjbenzyl-2,4-thiazolidinedione;

544-[3-(3,4-difluorophenyl)-2-oxooxazolidin-5-yl]-methoxy]benzyl-2,4-thiazolidinedione;

54443-(4-chloro-2-fluorophenyl)-2-oxooxazolidin-5-ljmethoxyjbenzyl 2,4thiazolidinedione;

5 5-[4-[3-(4-trifluoromethoxyphenyl)-2-oxooxazolidin-5-yl]methoxylbenzyl-Z4 thiazolidinedione;

544-[3-(4-triffuoromethylphenyl)-2-oxooxazolidin-5-yl] methoxylbenzyl-2,4-thiazolidinedione;

54442-[3-(4-trifluoromethylphenyl)-2-oxooxazolidin-5-yljethoxy]benzyl]-2,4-thiazolidinedione;

5444243-(4-chloro-2-fluorophenyl)-2-oxooxazolidin-5-yljethoxy]benzyli-0.4-thiazolidinedione;

54443-(4-pyridyl)-2-oxooxazolidin-5-yl]methoxyl-benzyl-2,4-thiazolidinedione;
4-(2-naphihyltnethyl)-1,2,3,5-oxathiadiazole-2-oxide;
15 544-424N-(benzoxazol-2-yl)-N-tnethyl amino}ethoxy]benzyl}-5-methylthiazolidine-2,4-dione;
5444242,4-dioxo-5-phenylthiazoliclin-3-ypethoxy]benzylithiazolidine-2,4-dione;
54442-1N-methyl-N-(phenoxyearbonypainino]ethoxy]benzyl]thiazolidine-Z4-dione;
5-[4-(2-phenoxyethoxy)benzyl]thiazolidine-2,4-dione;
54442-(4-chlorophenyDethylsulfonylibenzyllthiazolidine-2,4-dione;
5-[4-[3-(5-methyl-2-phenyloxazol-4-y0propionyl]benzyl-lthiazolidine-2,4-dione;
5-[[4-(3-hydroxy-1-methylcyclohexyptnethoxyjbenzylithiadiazolidine-2,4-dione;
54442-(5-methyl-2-phenyloxazol-4-yl)ethoxylibenzyl]thiadizolidione-2,4-dione;
5-[[2-(2-naphthylmetlayl)benzoxazol]-5-ylmethylitliiadiazoline-2,4-dione;
25 544[2-(3-phenylureido)ethoxyljbenzylithiadiazoline-2,4-dione;
54442-[N-(benzoxazol-2-yl)-N-methylamino]ethoxyThenzyjthiadiazoline-2,4-dione;
5 44-[3-(5-methyl-2-phenyloxazol-4-371)propionylThenzyl]thiadiazoline-174-dione;
5-[2-(5-methyl-2-phenyloxazol-4-ylmethyl)benzofuran-5-ylmethyl]-oxazolidine-2,4-dione;
54442-[N-methyl-N-(2-pyridyl)amino]ethoxylbenzylithiazolidine-2,4-dione;
54442-[N-(benzoxazol-2-yl)-N-methylaminoiethoxylbenzyl]-oxazolidine-2,4-dione and
54(64(2-fluorophenyl)methoxy)-2-naphthalenyl)methyl)-2,4-thiazolidinedione netoglitazone (MCC 555, MCC-555 or RWJ-241947; MITSUBISHI-TOKYO PHARMACEUTICALS).

Particular examples of thiazolidinediones that are used in the methods of the invention are the compounds conventionally known for the treatment of diabetes. See e.g., U.S. Pat. Nos. 4,812,570; 4,775,687; 4,725,610; 4,582,839; and 4,572,912 for exemplary sources of such compounds. U.S. Pat. No. 5,521,201 and European Patent Applications 0008203, 0139421, 0155845, 0177353, 0193256, 0207581 and 0208420; and Chem, Pharm, Bull 30 (10) 3580-3600 relate to thiazolidinedione derivatives, and describe commercial sources/synthetic schemes for a variety of STAT5 antagonist and STAT5 antagonist-like analogs, which may be useful in carrying out the combined preparation of the present invention. In some embodiments, thiazolidinedione compounds include: troglitazone, pioglitazone, rosiglitazone and netoglitazone.

In certain embodiments, the myeloid hemopathies are selected from the group consisting of acute myeloid leukemia (AML) and myeloproliferative/myelodysplasic disorders, including Chronic myelogenous leukemia (CML), Polycythemia Vera (PV), Essential thrombocythemia (ET), Chronic idiopathic myelofibrosis (Agnogenic myeloid metaplasia (AMM)), Chronic neutrophilic leukemia (CNL), Chronic eosinophilic leukemia/hypereosinophilie syndrome (CEL/I-JES) and systemic mastocytosis (SM). In a particular embodiment, the myeloid hemopathy is Chronic myelogenous leukemia (CML).

The STAT5 antagonist, e.g., PPARγ agonist and the anti-cancer agent are prepared in the form of pharmaceutical compositions suitable for oral administration. In some embodiments, the STAT5 antagonist, e.g., PPARγ agonist and the anti-cancer agent are in a single dosage form or as separate dosage forms suitable for oral administration (capsule(s), sachet(s), tablet(s)).

The combined preparation comprises an effective amount of the STAT5 antagonist, e.g., PPARγ agonist and of the anti-cancer agent. In certain embodiments, the combination is administered in an effective amount to achieve CMR.

The exact amount of STAT5 antagonist, e.g., PPARγ agonist and of the anti-cancer agent to be used in the combined preparation to be administered will vary according to factors such as the specific hyperplastic/cancer cell involved, and the specific disease; the degree of or involvement or the severity of the disease; the size, age, and general health of the patient; the response of the individual patient; the particular compound administered; the bioavailability characteristics of the preparation administered; the dose regimen selected; the kind of concurrent treatment; pharmacodynamic characteristics of the compounds and their mode and route of administration; and other relevant characteristics that the physician or as one skilled in the art, will readily determine by the use of known techniques and by observing results obtained under analogous circumstances.

In some embodiments, the present invention involves the administration of 300-400 mg of Imatinib and 30-50 mg of pioglitazone in a single dosage form or as separate dosage forms suitable for oral administration. In certain embodiments, the imatinib is first administered until a stable cumulative incidence of response is achieved, followed by a daily dose of a STAT5 antagonist (e.g., PPARγ agonist) until the patient achieves complete molecular remission (CMR).

Accordingly, the STAT5 antagonist, e.g., PPARγ agonist, and the anti-cancer agent may be administered concurrently or sequentially. In certain embodiments, the STAT5 antagonist, e.g., PPARγ agonist and the anti-cancer agent are concurrently administered to a patient having a myeloid hemopathy, the administration being performed to the time when a complete molecular response (CMR) is observed in the patient. Simultaneous administration is generally used for patients which respond poorly to the anti-cancer agent; the STAT5 antagonist, e.g., PPARγ agonist is used to potentialize the effect of the anti-cancer agent (e.g., by pulling the cancer stem cells of the myeloid lineage(s) out of quiescence, such that they are eliminated by the anti-cancer agent).

Accordingly, sequential administration generally comprises a first-line therapy with the anti-cancer agent until a suitable cumulative incidence of response is achieved. The STAT5 antagonist (e.g., PPARγ agonist), is then administered until a complete molecular response (CMR) is achieved, thereby preventing disease relapse by eliminating the residual cancer cells of the myeloid lineage(s). Sequential administration is generally preferred when the patient is a good responder (rapid and prolonged cytological response to the anti-cancer agent).

In another aspect, the invention provides a kit for carrying out the administration of the combined preparation as defined above, comprising a STAT5 antagonist or PPARγ agonist, as defined above and at least one anti-cancer agent, as defined above, as a single dosage form or as separate dosage forms.

The practice of the present invention employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M, AUSUBEL, 2000, Wiley and son Inc, Library of Congress, USA); Molecular Cloning: A Laboratory Manual, Third Edition, (Sambrook et al, 2001, Cold Spring. Harbor, N.Y.: Cold Spring Harbor Laboratory Press); Oligonueleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Blames & S, J. Higgins eds. 1984); Culture Of Animal Cells (R. L Freshney, Alan R. Liss, Inc, 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D, Goeddel, ed); Gene Transfer Vectors For Manunalian Cells (J. H. Miller and M. P. Calos eds., 1987, Cold Spring Harbor. Laboratory); Immunochemical Methods In Cell And Molecular. Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold. Spring Harbor Laboratory Press, Cold Spring Harbor, N.Y., 1986). Current Protocols in Human Genetics (John Wiley 10 & Sons, Inc, 2008), specifically Chapter 12 "Vectors For Gene Therapy" and Chapter 13 "Delivery Systems for Gene Therapy").

In addition to the preceding features, the invention further comprises other features which will be evident from the description which follows, and examples illustrating the use of the STAT5 antagonist, e.g., PPARγ agonist to maintain remission of hematologic cancers following standard cancer therapy.

1. Nguyen, L. V., Vanner, R., Dirks, P., Eaves, C. J. Cancer stem cells: an evolving concept. *Nat Rev Cancer* 12, 133-143 (2012).
2. Chomel, J. C., Turhan, A. G. Chronic myeloid leukemia stem cells in the era of targeted therapies: resistance, persistence and long-term dormancy. *Oncotarget* 2, 713-727 (2011).
3. de Lavallade, H., et al. Imatinib for newly diagnosed patients with chronic myeloid leukemia: incidence of sustained responses in an intention-to-treat analysis. *J Clin Oncol* 26, 3358-3363 (2008).
4. Graham, S. M., et al. Primitive, quiescent, Philadelphia-positive stem cells from patients with chronic myeloid leukemia are insensitive to STI571 in vitro. Blood 99, 319-325 (2002).
5. Copland, M., et al. Dasatinib (BMS-354825) targets an earlier progenitor population than imatinib in primary CML but does not eliminate the quiescent fraction. Blood 107, 4532-4539 (2006).
6. Corbin, A. S., et al. Human chronic myeloid leukemia stem cells are insensitive to imatinib despite inhibition of BCR-ABL activity. *J Clin Invest* 121, 396-409 (2011).
7. Luo, J., Solimini, N. L., Elledge, S. J. Principles of cancer therapy: oncogene and non-oncogene addiction. *Cell* 136, 823-837 (2009).
8. Prost, S., et al. Human and simian immunodeficiency viruses deregulate early hematopoiesis through a Nef/PPARgamma/STAT5 signaling pathway in macaques. *J Clin Invest* 118, 1765-1775 (2008).
9. Berria, R., et al. Reduction in hematocrit and hemoglobin following pioglitazone treatment is not hemodilutional in Type II diabetes mellitus. *Clin Pharmacol Ther* 82, 275-281 (2007).
10. Holyoake, T., Jiang, X., Drummond, M., Eaves, A., Eaves, C. Elucidating critical mechanisms of deregulated stem cell turnover in the chronic phase of chronic myeloid leukemia. *Leukemia* 16, 549-558 (2002).
11. Bonnet, D., Dick, J. Human acute myeloid leukemia is organized as a hierarchy that originates from a primitive hematopoietic cell. *Nat Med* 3, 730-737 (1997).
12. Wang, Z., Li, G., Tse, W., Bunting, K. D. Conditional deletion of STAT5 in adult mouse hematopoietic stem cells causes loss of quiescence and permits efficient nonablative stem cell replacement. *Blood* 113, 4856-4865 (2009).
13. Ilaria, R. L. Jr., Van Etten, R. A. P210 and P190(BCR/ABL) induce the tyrosine phosphorylation and DNA binding activity of multiple specific STAT family members. *J Biol Chem* 271, 31704-31710 (1996).
14. Nieborowska-Skorska, M., et al. Signal transducer and activator of transcription (STAT)5 activation by BCR/ABL is dependent on intact Src homology (SH)3 and SH2 domains of BCR/ABL and is required for leukemogenesis. *J Exp Med* 189, 1229-1242 (1999).
15. Nelson, E., et al. The STAT5 inhibitor pimozide decreases survival of chronic myelogenous leukemia cells resistant to kinase inhibitors. *Blood* 117, 3421-3429 (2011).
16. Hoelbl, A., et al. Clarifying the role of Stat5 in lymphoid development and Abelson-induced transformation. *Blood* 107, 4898-4906 (2006).
17. Hoelbl, A., et al. Stat5 is indispensable for the maintenance of bcr/abl-positive leukaemia. *EMBO Mol Med* 2, 98-110 (2010).
18. Walz, C., et al. Essential role for Stat5a/b in myeloproliferative neoplasms induced by BCR-ABL1 and JAK2 (V617F) in mice. *Blood* 119, 3550-3560 (2012).
19. Warsch, W., et al. High STAT5 levels mediate imatinib resistance and indicate disease progression in chronic myeloid leukemia. *Blood* 117, 3409-3420 (2011).
20. Wang, L., Giannoudis, A., Austin, G., Clark, R. E. Peroxisome proliferator-activated receptor activation increases imatinib uptake and killing of chronic myeloid leukemia cells. *Exp Hematol* 40, 811-819 (2012).
21. Chomel, J. C., et al. Leukemic stem cell persistence in chronic myeloid leukemia patients with sustained undetectable molecular residual disease. *Blood* 118, 3657-3660 (2011).
22. Laurie, C. C. et al. Detectable clonal mosaicism from birth to old age and its relationship to cancer. *Nat Genet* 44, 642-650 (2012).
23. Mahon, F. X., et al. Discontinuation of imatinib in patients with chronic myeloid leukaemia who have maintained complete molecular remission for at least 2 years: the prospective, multicentre Stop Imatinib (STIM) trial. *Lancet Oncol* 11, 1029-1035 (2010).
24. Ikezoe, T., et al. Inhibition of signal transducer and activator of transcription 5 by the inhibitor of janus kinases stimulates dormant human leukemia CD34+/CD38− cells and sensitizes them to antileukemia agents. *Int J Cancer* 128, 2317-2325 (2011).
25. Gough, D. J., et al. Mitochondrial STAT3 supports Ras-dependent oncogenic transformation. *Science* 324, 1713-1716 (2009).

The entire contents of the above publications are herein incorporated by reference in their entirety.

EXAMPLES

Materials and Methods

Reagents. For in vitro assays, PPARγ agonists were provided by Cayman Chemical (PPARγ-PAK; Bertinpharma). Imatinib mesylate was provided by Novartis and was used at 1 µM in culture, a well established inhibitory concentration in vitro that also approaches the achievable drug level in patients' plasma.

Cell culture and proliferation assays. K562 cells ($2 \times 10^5$) were cultured in 96-well plates, in complete Dulbecco's Modified Eagle medium supplemented with 10% fetal calf serum (Gibco®, Life technologies) alone or with variable concentrations of pioglitazone or troglitazone. Cells were cultured for 7 days in the presence of 1 µCi/well [$^3$H] thymidine, collected by centrifugation and counted on a plate reader (Wallac 1450 Microbeta Plus). Eight replicates were used for each set of conditions and results were obtained after three independents experiments. $CD34^+$ cells from patients in CP-CML at diagnosis or umbilical cord blood were immunoselected (CD34 microBead Kit, Miltenyi Biotec) according to the manufacturer's instructions. Enrichment for CD34+ cells was ascertained by flow cytometry using an anti-CD34 monoclonal antibody (clone 581; BD Pharmingen). $Ph1^+$-$CD34^+$ cells were cultured in serum free medium (SFM) StemSpan (StemCell Technologies) without growth factors.

Colony Forming Cell (CFC) and Long Term Culture—Initiating Cell (LTC-IC) assays. For CFC assays, $CD34^+$ cells were suspended ($1 \times 10^4$) in 3 ml of alpha-MEM based methylcellulose medium (GF H4434, Stemcell Technologies). Cells were scored and collected after 14 day incubation at 37° C. and 5% $CO_2$. After scoring, colonies were washed with PBS and kept frozen in RNAlater® (Invitrogen) for subsequent analysis. LTC-IC with limiting dilution assays (LDA) were performed in StemSpan SFEM medium (Stemcell technologies) on irradiated MS5 monolayers at several dilutions of $CD34^+$ cells (300, 150, 75, or 37 cells per well for $Ph1^+$ $CD34^+$ cells and 200, 100, 50, or 25 cells per well for $CD34^+$ from healthy donors) in 96-well plates with 16 replicate wells per concentration. After five weeks with weekly change of one half medium volume, all cells were transferred in alpha-MEM based methylcellulose medium (GF H4434, Stemcell technologies) to determine the total clonogenic cell content of each LTC. LTC-IC frequencies were determined using the L-Calc software (Stemcell technologies).

Flow cytometry. The following antibodies were used: fluorescein isothyocyanate (FITC)-conjugated IgG1 (clone 679.1Mc7, Beckman Coulter), Alexa Fluor® 488-conjugated-IgG1 (clone MOPC-21, BD Pharmingen), allophycocyanin (APC)-IgG1 (clone MOPC-21, BD Pharmingen), peridinin chlorophyll protein-cyanin 5.5 (PerCP-Cy5.5)-conjugated IgG1 (clone X40, BD Pharmingen), phycoerythrin cyanin (PE-Cy7)-conjugated IgG1 (clone MOPC-21, BD Pharmingen), (PerCP-Cy5.5)-conjugate CD45 (clone 2D1, BD Pharmingen), (APC)-conjugated CD34 (clone 581, BD Pharmingen), (PE-Cy7)-conjugated CD38 (clone HB7, BD Pharmingen), Alexa Fluor® 488-conjugated anti-STAT5 (pY694) (clone 47, BD Pharmingen), (PE)-conjugated anti-GLUT1 (FAB1418P, R&D systems). For all experiment, cell viability was assessed using SYTOX® Blue dead cell stain (Invitrogen Life Technologies).

Apoptosis assays. Annexin V conjugated to FITC and propidium iodide (PI) (Annexin-V kit, BD Pharmingen) were used to quantify apoptotic cells according to the manufacturer.

Intracellular STAT5 phosphorylation assays. In brief, $3.10^5$/ml K562 cells cultured in complete Dulbecco's Modified Eagle medium supplemented with 10% fetal calf serum (PAA) alone and with or without pioglitazone (10 µM) or Imatinib (1 µM) at 37° C. in 5% $CO_2$ were harvested at variable time as indicated. Cells were fixed and permeabilized using Cytofix/Cytoperm kit (BD Pharmingen) and stained with Alexa Fluor® 488-anti-phospho-STAT5 mAb (BD Phosflow) or Alexa Fluor® 488-isotype-matched control to obtain fluorescence minus comparative in each experiment. Analysis was carried on a minimal number of 50,000 events in the viable cell gate. The delta mean fluorescence intensity of p-STAT5 after drug treatment (p-STAT5ΔMFI) was determined as follow: (untreated cells p-STAT5 MFI-non treated cells isotype-control MFI)-(drug treated cells p-STAT5 MR-drug treated cells isotype-control MFI).

CSFE assays. Fresh $CD34^+$-enriched cells were stained with 2 µM of 5-(and 6-) carboxyfluorescein diacetate succinimidyl diester (CFSE, Invitrogen). Cells were then cultured (seeded $5.10^5$/mL) in SFM StemSpan (StemCell Technologies) without growth factors and with or without pioglitazone (10 µM) or Imatinib (1 µM). Cells cultured in the presence of Colcemid® (100 ng/ml, Invitrogen Life Technologies) were used to establish the range of fluorescence exhibited by cells that had not divided during post-labeling incubation. Cells were harvested at variable time points as indicated, collected in BD Trucount™ tubes for absolute count (BD Biosciences) and labeled with anti-CD45 and anti-CD34. Then, cells were diluted in 1 mL of phosphate-buffered saline (PBS, Invitrogen Life Technologies) containing 2% fetal calf serum (PAA) and stained for viability. All analyses were carried out on a BD FACS Canto2 Flow Cytometer.

RNA extraction and RT-qPCR analysis. RNA was extracted from $2 \times 10^5$ cells using RNAqueous-4PCR (Ambion). Reverse transcription was carried out for 1 hour at 42° C. using SuperScript® Vilo™ cDNA Synthesis kit (Invitrogen Life Technologies) according to the manufacturer's instructions. Real-time PCR was performed in an iCycler thermocycler (CFX, Bio-Rad). The primer pairs used with Taqman® Gene Expression Master mix (Applied Biosystems) and iQ Supermix SYBR GRN (Bio-Rad) are listed in Table 2a and Table 2b, respectively. The comparative CT method (ΔΔCT) was used to compare gene expression levels between the different culture conditions (relative to GAPDH).

Western blot analysis. For STAT5 protein analysis, K562 cells ($2.5 \times 10^5$) were lysed in RIPA lysis buffer on ice. Whole-cell extracts were boiled for 5 minutes in Laemmli sample buffer and subjected to SDS-PAGE in 4-12% acrylamide gels (Nupage, Invitrogen Life Technologies). Proteins were transferred to Hybond N+ filters (Amersham). Membranes were probed with the following antibodies: STAT5 (sc-1656), actin (sc-8432), and goat anti-mouse IgG-HRP (sc-2005) (Santa Cruz Biotechnology Inc.). Antibody binding was detected by the enhanced chemiluminescence ECL+ (Amersham).

Lentiviral vector production and transduction. STAT5B lentiviral vector. The cDNA encoding STAT5B was cloned, sequenced (Genbank acquisition number DQ267926), and inserted into the SIN-cPPT-PGK-WHV lentiviral transfer vector as previously described. A SIN-cPPT-PGK-eGFP-WHV lentiviral vector was used for control.

shRNA lentiviral vector anti-PPARγ. The PPARγ mRNA pairing sequence 5'-TGTTCCGTGACAATCTGTC-3' (Genbank accession number HUMPPARΓB) was designed and synthesized as follows within an shRNA structure comprising unique restriction sites at each end: sense 5'-GATCTCCTGTTCCGTGACAATCTGTCT-TCAAGAGA ACAGATTGTCACGGAACATTTTTG-GAAGAATTCC-3'; antisense 5'-CTGAG GAATTCTTC- CAAAAATGTTCCGTGACAATCTGTAAGTTCTCTACA GATTGTCA CGGAACAGGA-3'. Oligonucleotides were annealed and ligated into BglII and XhoI sites of linearized pSuper plasmid. PolIII H1 promoteur-shRNA PPARγ was then subcloned in the pTRIP lentiviral vector. Vectors were produced as previously described.

BCR-ABL lentiviral vector. Total RNA from K562 cells was extracted using TRIZOL (Invitrogen Life Technologies). Reverse transcription was carried out for 1 hour at 50° C. using SuperScript® III (Invitrogen Life Technologies). Two independent PCR were performed using BCR-ABL F 1, 5'-ATGGTGGACCCGGTGGGCTT-3' with BCR-ABL R 2831, 5'-CTGCTACCTCTGCACTATGTCACTG-3' and BCR-ABL F 2685, 5'-TCCGCTGACCATCAATAAGGA-3' with BCR-ABL R 6097, 5'-CTGCTACCTCTGCACTAT-GTCACTG-3' respectively. Specific amplification bands were pooled, heated to 95° C. during 3 minutes and ramp cooled to 25° C. over a period of 45 minutes. Annealing product was submitted to a third PCR with LA Taq™ DNA polymerase (Takara) using the following primer pair: BCR-ABL F 1 asci: 5'-AGGCGCGCCATGGTGGACCCG-GTGGGCTT-3' and BCR-ABL R 6097 sbf1: 5'-CCTGCA-GGCTGCTACCTCTGCACTATGTCACTG-3'. Amplification product was subcloned into a pCR®-XL-TOPO® plasmid (Invitrogen Life Technologies) before being inserted into the SW GAE-SSFV lentiviral transfer vector, followed by DNA sequencing. An SIV GAE-SSFV-eGFP vector was used as a control. The SIV vectors were produced as previously described.

CD34+ cell transduction. Cells were suspended (1×10⁶/ml) in StemSpan (StemCell Technologies, France) supplemented with protamine sulfate (4 µg/ml), SCF (100 ng/ml), Flt-3-L (100 ng/ml), IL-3 (20 ng/ml), and IL-6 (20 ng/ml), in a 96-well plate coated with RetroNectin® (Takara Shuzo Co., Japan). Cell suspensions were incubated for 16 hours. Lentiviral vectors were then added and cell suspensions incubated for 12 hours. Cells were washed twice before being seeded.

siRNA assays. siRNA targeting the human PPARγ sequence 5'-TGTTCCGTGACAATCTGTC-3' were synthesized (Sigma-Aldrich Proligo). CD34+ BM cells were transfected with PPARγ-specific siRNA (25 nM) or control siRNA in the presence of Lipofectamine 2000 (Invitrogen) and maintained for 48 hours before CFC assay. Control siRNA was purchased from Invitrogen Life Technologies (BLOCK-iT). Transfection efficiency was assessed using a fluorescein-labeled, double-strand RNA duplex (BLOCK-iT FluorescentOligo; Invitrogen).

Human patients. Fresh bone marrow from patients with chronic-phase CML at diagnosis, umbilical cord blood cells from healthy donors, and blood or bone marrow samples from diabetes patients and patient given pioglitazone off-label were obtained with informed consent approved by the hospital's Institutional Review Board (<<Comité de protection des personnes Ile-de-France XI>>) under approved protocol EudraCT number: 2009-011675-79.

Statistical analysis. For culture assays and quantitative real-time PCR, values were calculated as mean±standard deviation for at least three separate experiments performed in triplicate. Specific number of samples and repeated experiments are indicated in the legends to Figures. Paired and unpaired comparisons were made, using the nonparametric Wilcoxon rank test and the Mann & Whitney test, respectively. Limiting dilution analysis was carried out with L-Calc software (StemCell Technologies). All statistical analyses were carried out with StatView software (SAS Institute Inc., Cary, N.C.).

Negre, D. et al. Characterization of novel safe lentiviral vectors derived from simian immunodeficiency virus (SIV-mac251) that efficiently transduce mature human dendritic cells. *Gene Ther* 7, 1613-1623 (2000).

Example 1

It was first determined that the anti-proliferative effect of two different STAT5 antagonists onto K562 cells follows a graded dose-response curve, one indicator of target specificity (FIG. 5a). Specificity was further supported by inclusion of a shRNA against PPARγ mRNA (FIG. 5b). Umbilical cord blood CD34+ cells from healthy donors were then transduced with a lentiviral vector expressing p210 BCR-ABL.

Results

Figure 5:
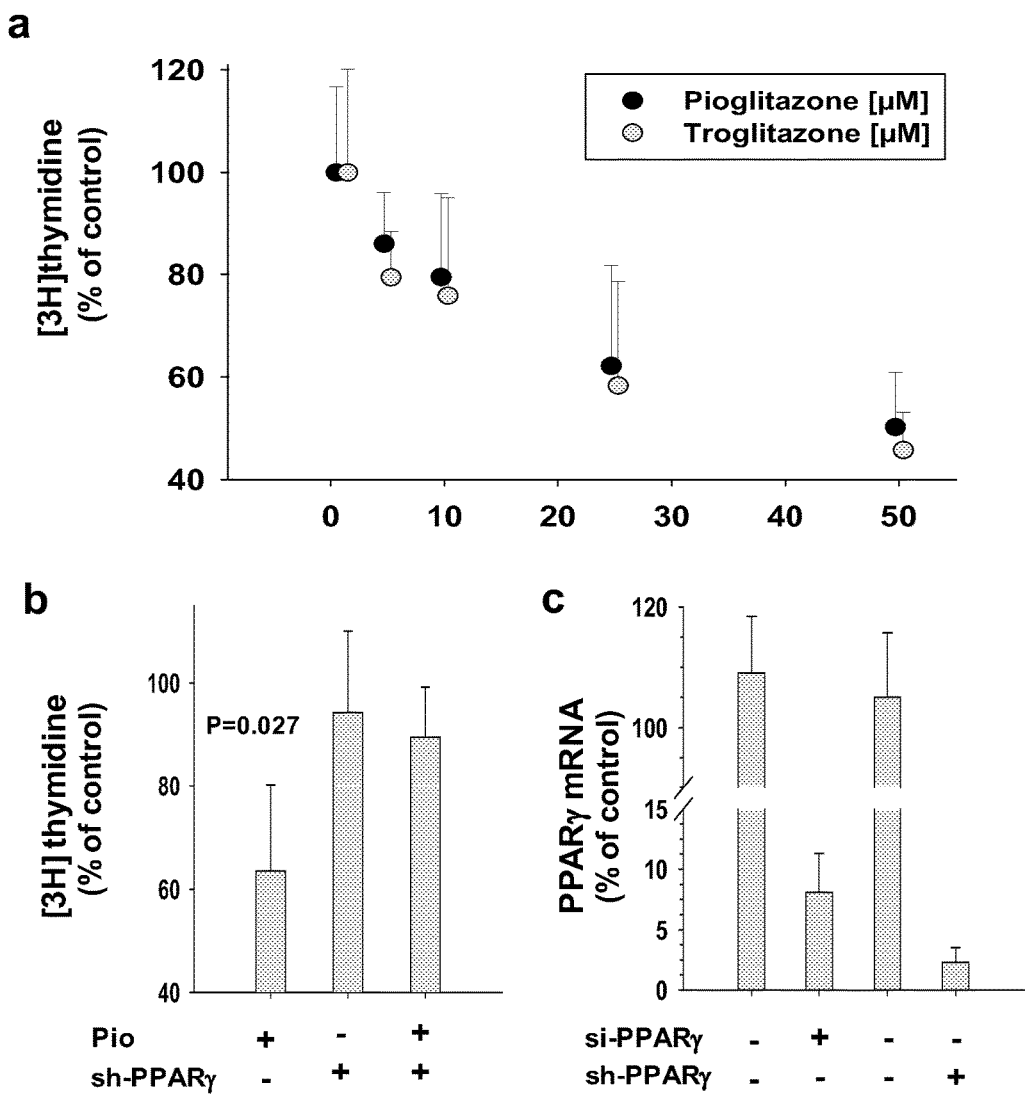
FIG. 5 (a)-(c) shows the specificity of STAT5 antagonist action in BCR-ABL expressing cells through PPARγ.

FIG. 5 depicts specificity of STAT5 antagonist action in BCR-ABL expressing cells through PPARγ. a, Dose-response curves of two STAT5 antagonists onto K562 cell proliferation evaluated by [³H]thymidine incorporation for 7 days (3 experiments, 8 replicates for each). b, Differential K562 cell proliferation, with or without exposure to pioglitazone (25 µM), and with or without lentivector-mediated expression of an sh-RNA against PPARγ mRNA (sh-PPARγ) (3 experiments). c, Verification of the specificity of the sh-PPARγ lentivector used in FIG. 5b. CD34+ cells were transfected with irrelevant or PPARγ targeting si-RNA (25 nM each) or transduced with the sh-PPARγ or an eGFP lentivector. PPARγ transcripts were normalized to GAPDH transcripts and expressed relative to the levels measured in untransfected/untransduced cells.

Example 2

From the in vitro studies above, it was demonstrated that pioglitazone at pharmacological doses inhibits cell growth of the Bcr-Abl positive cell line K562 through the activation of the PPARγ/STAT5 pathway. Further in vitro studies were performed which showed that, in the presence of pioglitazone, the degree of reduction in colony forming cells (CFC) was 1.9-fold greater (p<0.002) when BCR-ABL was expressed (FIG. 1a). Combining pioglitazone and imatinib yielded a 3-fold (p<0.0001) inhibitory effect (FIG. 1a).

Results

FIG. 1 depicts differential and synergistic effects of pioglitazone and imatinib on CML cells. a, CFC assays after lentivector-mediated expression of BCR-ABL or eGFP (negative control) in human cord blood CD34+ cells. Means of 3 individuals in triplicate with standard deviation (SD). b, CFC assays with CD34+ CP-CML cells from patients at diagnosis. Means of 29 patients with SD. c, CD34+ CP-CML cells in liquid culture (7 days) in serum-free medium without cytokines. Seven patients, each scored as percentage of its own untreated control (see Table 1). d, Kinetics (Patient 4 of FIG. 1c). In all CFC assays, imatinib and/or pioglitazone were added for 48 h prior.

Example 3

A cohort of 29 chronic phase (CP) CML patients at diagnosis whose CD34+ cells were >90% Ph1+ was tested. The observed clonogenic defect was similar to that described in Example 2, but the effect of the drug combination was more pronounced (6-fold, p<0.0001) (FIG. 1b). In liquid culture of CP-CML CD34+ cells in the absence of cytokines, a similar trend was observed, although with low and high responders (7 patients tested) for the single agents (FIG. 1c and Table 1). However, when imatinib and pioglitazone were combined, the response was greater and less dispersed (FIG. 1c).

CML LSCs are generally phenotypically undistinguishable from normal human HSCs and are not readily transplantable in immunodeficient mice. Long Term Culture-Initiating Cell (LTC-IC) assays can be a suitable approach for CML LSC quantification.

accumulation of viable $CD34^+$ cells that never divided or had divided only once (34% vs. 5% for the untreated control) (FIG. 2d). Absolute cell count analysis was conducted and indicated that this phenomenon can be caused by both (1) a resistance of quiescent CML cells to the cytotoxicity of imatinib and (2) an anti-proliferative effect of imatinib that decreases the rate at which CP-CML $CD34^+$ cells exit quiescence and proceed with further cell divisions (FIG. 2e).

TABLE 1

Liquid culture of $CD34^+$ CP-CML cells from 7 patients

| Patient | Starting CD34 (%) | CD34 Sort (%) | Ctrl D 3 Fold exp | Ctrl D 3 viab (%) | Imatinib D 3 Fold exp | Imatinib D 3 viab (%) | Pio D 3 Fold exp | Pio D 3 viab (%) | Imatinib + Pio D 3 Fold exp | Imatinib + Pio D 3 viab (%) | Ctrl D 7 Fold exp | Ctrl D 7 viab (%) | Imatinib D 7 Fold exp | Imatinib D 7 viab (%) | Pio D 7 Fold exp | Pio D 7 viab (%) | Imatinib + Pio D 7 Fold exp | Imatinib + Pio D 7 Viab (%) |
|---|---|---|---|---|---|---|---|---|---|---|---|---|---|---|---|---|---|---|
| 1 | 4.70 | 81.20 | 1.81 | 28.00 | 0.03 | 0.1 | 0.75 | 19.00 | 0.03 | 0.01 | 1.39 | 41.00 | 0.01 | 0.10 | 0.39 | 9.00 | 0.00 | 0.00 |
| 2 | 1.80 | 71.00 | 1.48 | 59.00 | 0.67 | 31.00 | 1.25 | 47.00 | 0.68 | 27.00 | 5.8 | 87.00 | 0.94 | 29.70 | 2.96 | 71.00 | 0.29 | 13.00 |
| 3 | 1.50 | 78.40 | 0.62 | 18.00 | 0.13 | 4.10 | 0.27 | 9.90 | 0.08 | 2.20 | 1.89 | 18.30 | 0.45 | 5.90 | 1.69 | 17.90 | 0.09 | 4.10 |
| 4 | 13.4 | 98.00 | 1.69 | 92.4 | 1.14 | 86.00 | 2.02 | 93.00 | 1.16 | 82.00 | 2.41 | 52.30 | 1.26 | 54.00 | 1.67 | 54.00 | 0.92 | 47.50 |
| 5 | 1.10 | 70.00 | 1.16 | 73.00 | 0.53 | 54.5 | 1.32 | 73.00 | 0.35 | 42.00 | 1.66 | 86.00 | 0.49 | 56.00 | 0.93 | 86.00 | 0.22 | 53.00 |
| 6 | 3.00 | 96.70 | 1.95 | 90.20 | 1.09 | 85.00 | 1.69 | 88.00 | 0.86 | 83.00 | 1.83 | 74.00 | 1.49 | 73.00 | 1.87 | 85.00 | 0.50 | 60.00 |
| 7 | 3.4 | 88.00 | 1.21 | 87.00 | 0.60 | 84.00 | 0.86 | 84.00 | 0.52 | 83.00 | 4.94 | 40.00 | 1.38 | 66.00 | 1.48 | 33.00 | 0.60 | 55.00 |
| | | mean | 1.42 | | 0.60 | | 1.17 | | 0.53 | | 2.85 | | 0.86 | | 1.54 | | 0.36 | |

CTRL: control cells without drug, D 3: Day 3 in culture, D 7: D 7 in culture, Pio: pioglitazone, Sort: percentage after cell sorting, viab: viable cells, exp: expansion.

Example 4

Imatinib alone was unable to reduce significantly the frequency of CP-CML LTC-ICs (p=0.067 and p=0.02). However, pioglitazone was able to do so, either as a single agent by 2.4-fold (p=0.008) or with a synergic effect by 3.5-fold in the presence of imatinib (p<0.001) or 5-fold in the presence of dasatinib ((p=0.0038) (FIGS. 2a and b). Pioglitazone had an effect opposite to imatinib onto cell cycle status by triggering exit from quiescence and a greater rate of cell proliferation (FIG. 2c-e). Moreover, combining pioglitazone and imatinib largely counteracted the deleterious effects of imatinib on cell cycle status and thus effectively acted in synergy to deplete both proliferating and non-proliferating cells (FIGS. 2d and e).

Results

Figure 2:
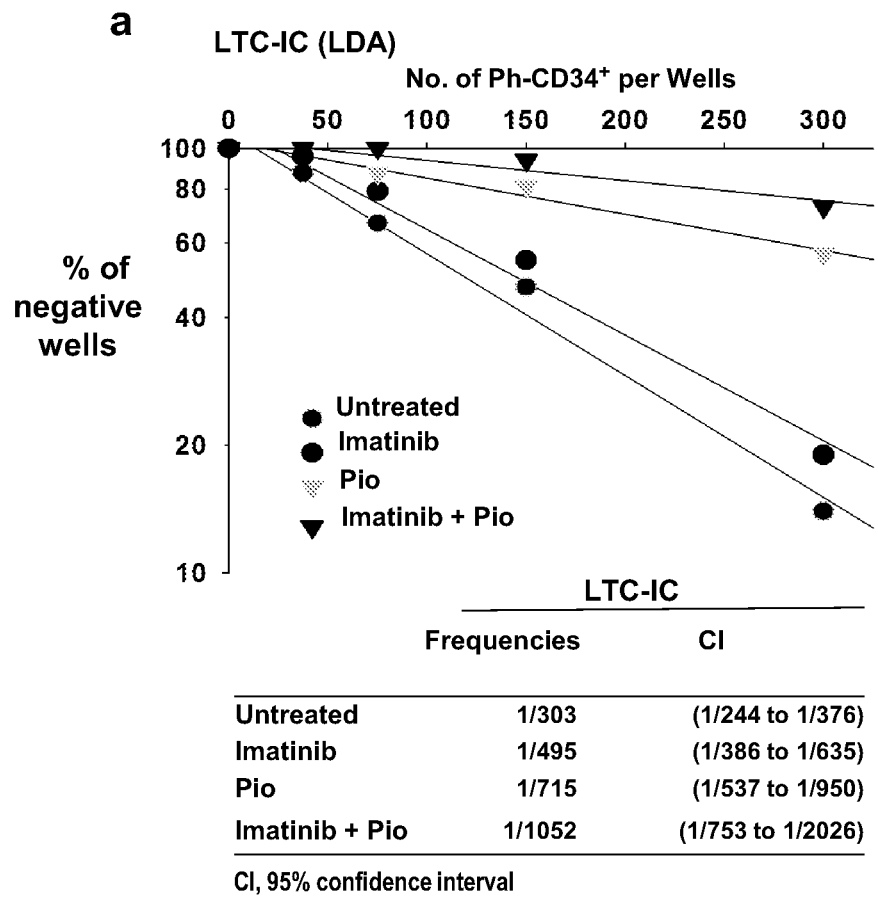
FIG. 2(a)-(e) shows quiescent CML stem cell (LSC) purging by pioglitazone.

FIG. 2 depicts quiescent CML LSC purging by pioglitazone. a and b, Limiting dilution analysis (LDA) with LTC-IC assays and LTC-IC frequencies calculated. Numbers of $CD34^+$ seeded are indicated. a, for 4 of the 7 patients (16 replicates for each), in the presence of imatinib. b, for 1 patient (16 replicates), in the presence of dasatinib. c, CFSE analysis (Patient 4) after liquid culture in serum-free medium without cytokines. One shaded peak for each cell division number. P, colchemid arrested "parent-cells". d, Distribution (%) of $CD34^+$ cells in each division peak shown in FIG. 2c. e, Identical culture conditions but for Patient 2 and absolute cell count. Left scale, total cells showing $CD34^+$ vs. $CD34^-$ cells (histograms). Right scale, undivided $CD34^+$ cells (dots and lines).

Cell cycling status is another criterion to assess or predict whether CML LSC purging may be effective. CFSE assays were performed with CP-CML $CD34^+$ cells in liquid culture lacking cytokines (FIG. 2c). Data were analyzed both as percentages (FIG. 2d) and absolute counts (FIG. 2e) of cells that never divided ("P") or underwent a given number of divisions. Untreated control CP-CML $CD34^+$ cells proliferated and differentiated actively. Imatinib exposure resulted in the elimination of actively dividing cells but also in the Example 5

The possible molecular pathways that mediate pioglitazone activity against CML LSCs were investigated. Signal Transducer and Activator of Transcription 5 (STAT5) was a target to consider. PPARγ can be a negative transcriptional regulator of STAT5 (A and B), and can cause a clonogenic defect in HIV and SIV infected hosts. STAT5 (A and B) can be critical for maintenance and fitness of normal HSCs in mice in an allele dose-dependent manner. In CML cells, STAT5 activation is dependent on the activity of the BCR-ABL kinase, while knock-down of STAT5 expression or inhibition of its phosphorylation suppress CML cell resistance to apoptosis and cytokine independence in vitro. Abrogation of STAT5 can prevent initiation and maintenance of a CML state otherwise triggered by retroviral transfer of BCR-ABL. STAT5 expression levels correlate with the degrees of disease progression in mouse models and initial TKI sensitivity in humans.

Results

Figure 3:
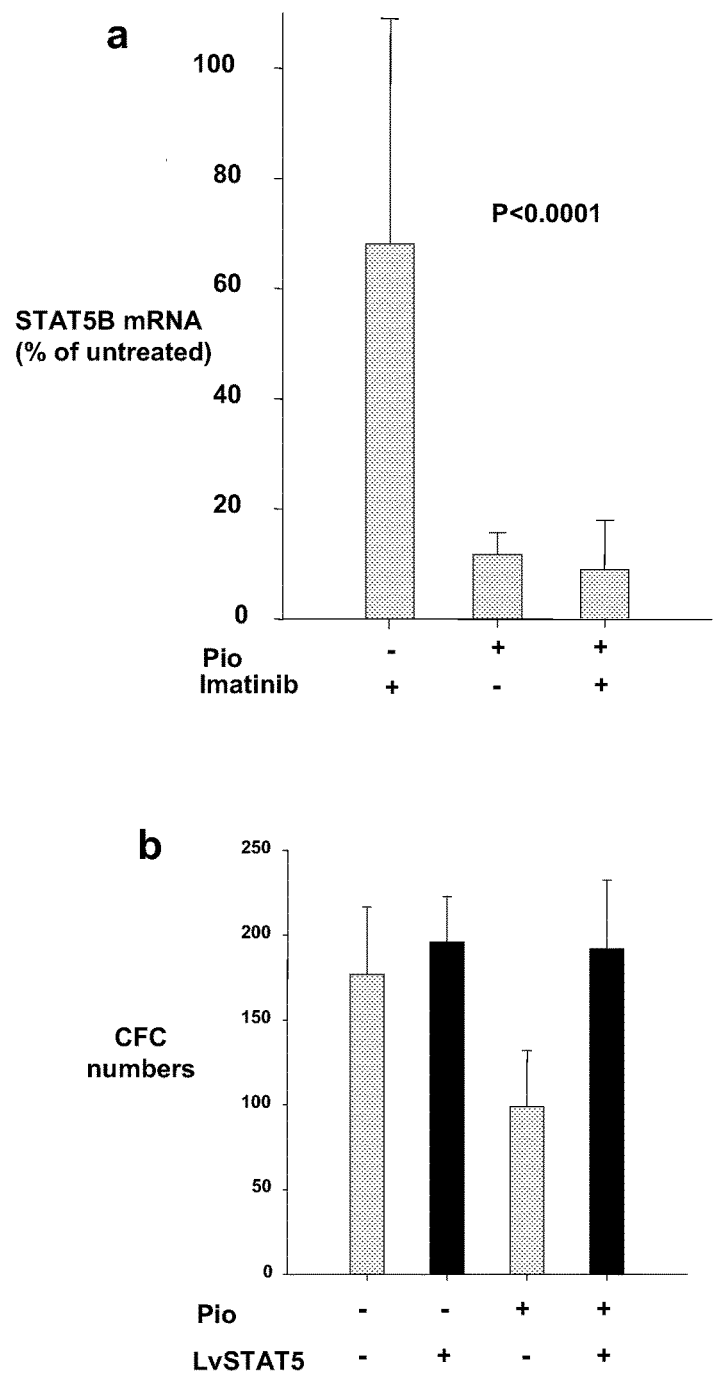
FIG. 3(a)-(f) shows the PPARγ-STAT5 pathway as target of pioglitazone in CML LSCs.

FIG. 3 depicts PPARγ-STAT5 pathway as target of pioglitazone in CML LSCs. a, Cultures as in FIG. 2e at Day 10. STAT5B RT-qPCR normalized to GAPDH mRNA (5 replica with SD). b, CFC assays with STAT5B or eGFP lentivectors in $CD34^+$ CP-CML cells. Means of 5 patients with SD. c, K562 cells. Same RT-qPCR as in FIG. 3a. si-PPARγ, siRNA against PPARγ mRNA. Means of 6 replica with SD. d, Flow cytometry of permeabilized K562 cells with IgG against phosphorylated (Tyr694) STAT5. Untreated (black ouline) and drug treated (grey shaded or grey outlined). Control panel, No drug treatment but irrelevant IgG isotype control (gray peak). Top right, Western blot analysis with pan-STAT5 and anti-actin antibodies, showing a decrease of STAT5 by 3.2-fold (normalized) in Lane 4. e, CFSE assays with STAT5B or eGFP lentivectors in $CD34^+$ CP-CML cells and absolute cell count as in FIG. 2e. Black dots, Undivided $CD34^+$ cells. Right panel, STAT5B lentivector control. f, LTC-IC (LDA) showing increased toxicity of pioglitazone for CP-CML vs. normal $CD34^+$ cells.

It was found that STAT5B mRNA levels were decreased by 8.5-fold ($p<0.0001$), 1.5-fold ($p=0.08$) and 10.5 fold ($p<0.0001$) in the presence of pioglitazone, imatinib and the drug combination, respectively, in CP-CML cells after 10 days of liquid culture without cytokines (FIG. 3a). Similar values were obtained for STAT5A. Decreased clonogenicity of CP-CML $CD34^+$ cells in the presence of pioglitazone was abolished when STAT5B was overexpressed after lentiviral transfer (FIG. 3b). Decrease of STAT5B mRNA levels was also observed in K562 cells, and this effect was negated by a siRNA against PPARγ mRNA (FIG. 3c). Because the kinetics of cytotoxicity is slower with pioglitazone alone than in the presence of imatinib (FIG. 1d), their differential mechanisms of action on STAT5 activity were investigated. It was found that imatinib acts rapidly (minutes) by preventing STAT5 phosphorylation whereas pioglitazone acts slowly (days) by decreasing STAT5 protein levels (FIG. 3d). The capability of pioglitazone both to pull CP-CML cells out of quiescence and to be cytotoxic, as assessed by absolute cell counts in CFSE assays, was completely abrogated when STAT5B was overexpressed by lentiviral transfer (FIG. 3e). Importantly, pioglitazone was found to be more inhibitory/cytotoxic for CML LTC-IC than for normal LTC-ICs (FIG. 3f).

Example 6

Figure 6:
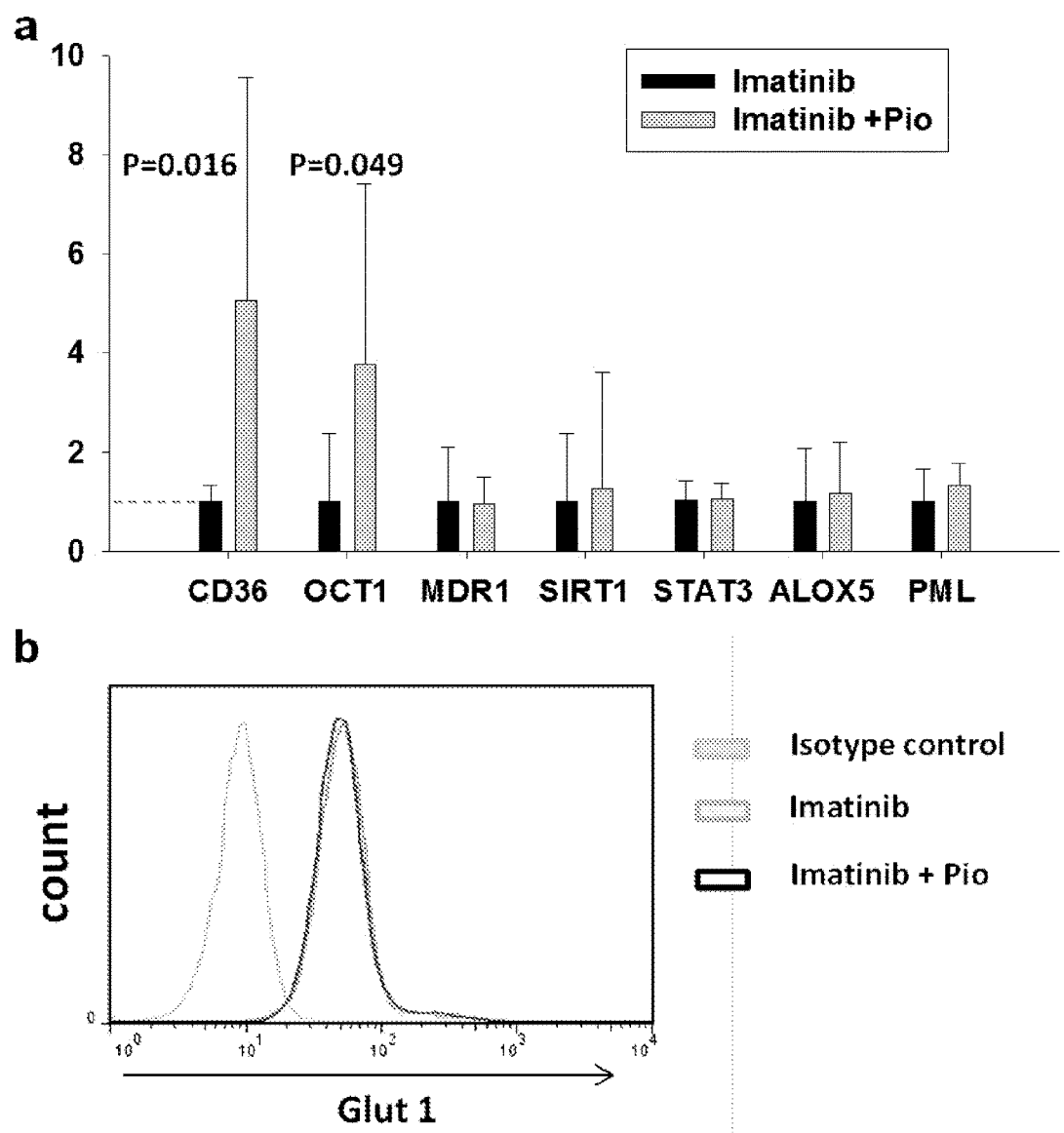
FIG. 6 (a)-(b) shows expression of target genes in CP-CML cells in response to pioglitazone and imatinib combination.

Cultures without cytokines of CP-CML $CD34^+$ cells from 10 patients were examined, with mRNA expression levels of 7 putative downstream transcriptional targets of STAT5 and/or PPARΓ relevant to CML LSCs, after exposure to imatinib, with or without pioglitazone, for 10 days. These include STAT5, SIRT1, GLUT1, OCT1, PML1, MDR1 and ALOX5. It was found that only OCT1 mRNA levels were moderately (3.75 fold; $p=0.049$) increased after culture in the presence of pioglitazone+ imatinib vs. imatinib alone (FIG. 6). Upregulation of OCT1 expression may increase the cellular uptake of imatinib, although CML LSCs are known to be weakly dependent upon BCR-ABL kinase activity.

Results

Figure 4:
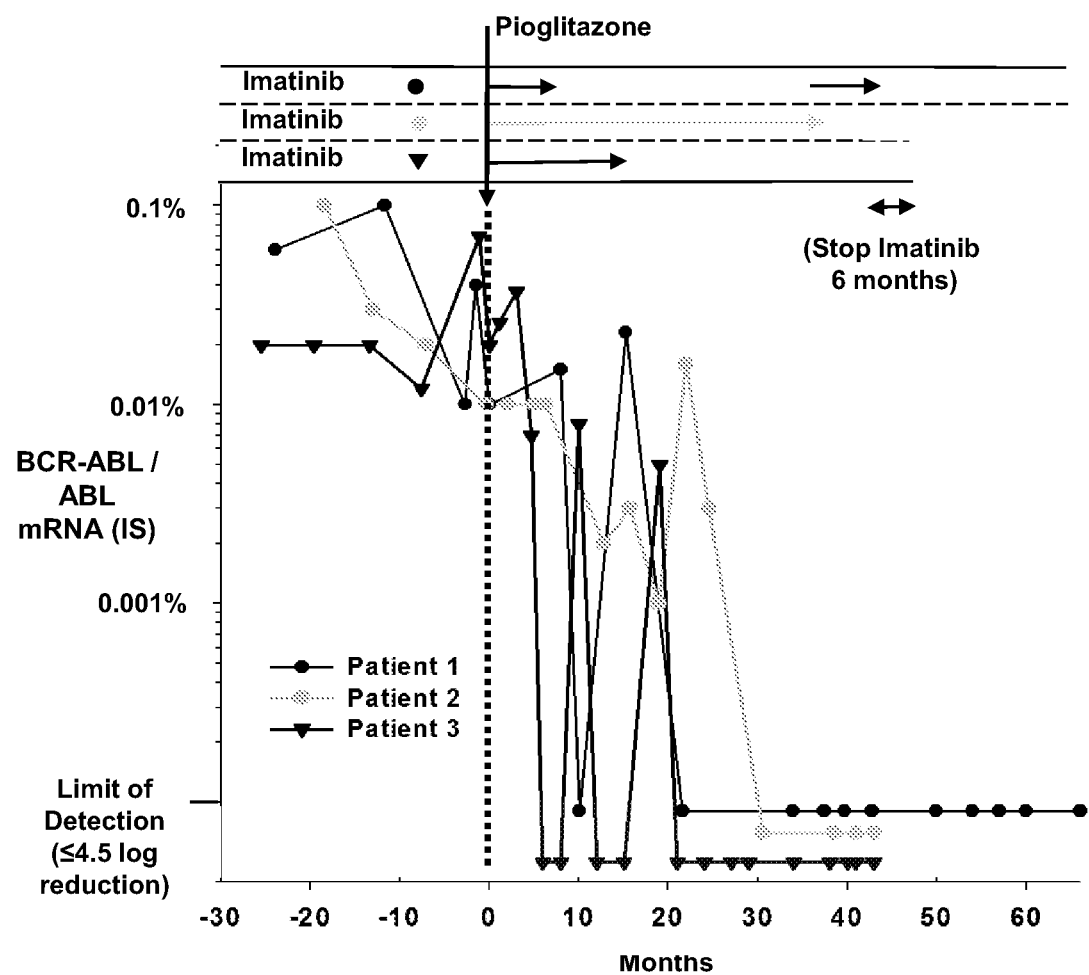
FIG. 4 shows pioglitazone-induced CMR in CML patients and maintenance after drug withdrawal.

FIG. 4 depicts pioglitazone-induced CMR in CML patients and maintenance after drug withdrawal. RT-qPCR assays for BCR-ABL/ABL on patients' nucleated blood cells at international (IS) ratios. Three patients showed sustained presence of BCR-ABL $mRNA^+$ blood cells for 3 to 6 years despite continuous imatinib therapy (grey blocks) received pioglitazone at t=0 for various durations (horizontal arrows). Pioglitazone treatment was stopped 18 to 54 months ago, although Patient 1 resumed treatment briefly for diabetes. Patient 2 withdrew after 1 year CMR. Patient 3 also stopped imatinib treatment without molecular relapse for 6 months. All patients reached CMR(4.5 log) for >12 to 56 months.

Patient 1 was diagnosed with a low Sokal score CML at age 62 in 2002, when imatinib was initiated (300-400 mg/day—plasma levels 924 ng/ml). A major molecular response was achieved after 17 months of therapy, but she never reached CMR (BCR-ABL/ABL mRNA IS ratios between 0.01% and 0.04%). Pioglitazone 30 mg/day was initiated by her endocrinologist in June 2007 after 5 years of imatinib therapy. Pioglitazone was temporarily stopped in April 2008, and briefly resumed from August 2010 to April 2011 for her diabetes. Unexpectedly, CMR(Slog) was achieved in June 2008, and she remains in CMR(Slog) since 56 months ago (FIG. 4). Patient 2 was diagnosed with a high Sokal score CML at age 61 in 2002, when imatinib was initiated (300-400 mg/day—plasma levels 310 ng/ml). The best molecular level of response was 0.02%. In March 2008, after 6 year of imatinib therapy, pioglitazone 30 mg/day was initiated. CMR(Slog) was obtained in August 2010 and maintained for 12 months at which time she withdrew (FIG. 4). Before filing a formal clinical trial application, pioglitazone was prescribed to a third CML patient. Patient 3 was diagnosed with a low Sokal score CML at age 58 in 2005, when imatinib was initiated (400 mg/day—plasma levels 790 ng/ml). His best BCR-ABL/ABL IS ratios were between 0.012% and 0.07%. Pioglitazone was initiated in December 2009 (45 mg/day). He reached CMR(Slog) after 6 months pioglitazone therapy, which was stopped in April 2011. He has remained in CMR(Slog) ever since (total of 28 months) (FIG. 4).

In a recent report, BCR-ABL mRNA expressing cells have been detected at high frequencies by CFC assays performed with bone marrow $CD34^+$ cells harvested from the rare CML patients in CMR for many years (>11 years) after imatinib and/or interferon treatment. Here, it was found that BCR-ABL mRNA expression was detectable but not quantifiable by RT-qPCR in CFC pools from Patient 3 having reached CMR(Slog) 1 year after initiation of pioglitazone.

Subsequent trials can be performed to confirm whether patients remain in CMR after discontinuing both imatinib and pioglitazone, given that greater than 50% patients in CMR for 2 years relapse one year after stopping TKIs.

The foregoing examples indicate that CML LSCs have a "non-oncogene addiction" to STAT5, as previously proposed in mouse models. This is likely distinct from the canonical BCR-ABL-mediated activation of STAT5 in the bulk of more differentiated CML cells. CML LSCs may be especially sensitive to STAT5 levels for their entry into cell cycle or dependent upon a yet unidentified function of STAT5, reminiscent of the accessory mitochondrial role played by STAT3 in oncogenesis.

Example 7

Twenty seven patients were enrolled in the clinical trial and 24 were evaluable (1 was excluded in CMR4.5, 1 patient was not in MMR and 1 patient had consent withdrawal). Median age was 61.6 years (24.1-79) and median follow-up after inclusion was 13 months (9.8-21). All evaluable patients started pioglitazone as planned. Seven patients (29.2%) discontinued pioglitazone before 12 months, no patient discontinued due to adverse events. Discontinuations occurred between month 3 and month 9. Median duration of pioglitazone therapy was 11.2 months (2.6-15.4) median daily dose was 39.9 mg. No interaction was observed between imatinib and pioglitazone in term of through level before (median 850 ng/ml) and after (median 927 ng/ml) pioglitazone initiation (p=ns). Main adverse events were weight gain and worsening fluid retention in 3 patients. Three patients (14%) obtained a confirmed undetectable level of BCR-ABL transcript. The one year cumulative incidence of CMR4.5 was 57%. Stat5 mRNA quantification was significantly diminished in patient samples at M6 and M12 compared to the baseline values and a reduction of the clonogenic potential was also observed in bone marrow cells at M6 and M12. "Control patients" were collected with similar characteristic (n=20). The cumulative incidence of CMR4.5 in this control group was 27% as compared to 57% in the pioglitazone group ($p=0.02$).

Results

FIG. 6 depicts expression of target genes in CP-CML cells in response to pioglitazone and imatinib combination. a, CP-CML CD34+ cells were cultured in serum-free medium without cytokines for 7 days with either imatinib alone (1 μM) or imatinib and pioglitazone (1 μM and 10 μM respectively). Cells were then processed for RT-qPCR assays with primers and probes specific for human OCT1, MDR1, SIRT1, STAT3, ALOX5 and PML1 CD36, known to be up regulated by PPARγ agonists, was used as a positive control. Results are normalized to GAPDH mRNA levels and represented relative to mRNA expression for the "Imatinib alone" condition (means of 11 patients with SD for each gene assessed). b, Cell surface expression of GLUT1 was quantified by flow cytometry (mean of 5 patients).

It was observed that PPARγ/STAT5 pathway induced a clonogenic defect in CD34+ cells from CML patients. Moreover, the activation of the PPARγ/STAT5 pathway also induced a clonogenic and a proliferative defect in CML LTC-IC. It was then confirmed that imatinib induced a selection of insensitive quiescent CML cells and showed that this effect was abrogated by the activation of the PPARγ/STAT5 pathway.

TABLE 2

Primers and probes used for RT-qPCR

| a Name | Primer and probe sequences | Modification | Conc |
|---|---|---|---|
| GAPDH F | 5'-TCGTGGAAGGAC TCATGACC-3' | | 900 nM |
| GAPDH R | 5'-TCAGCTCAGGGA TGACCTTG-3' | | 900 nM |
| GAPDH P | 5'-AGTCCATGCCAT CACTGCCACCCA-3' | 5'-[5HEX]3'-[BHQ1a~5HEX] | 250 nM |
| STAT5B F | 5'-GGCAGAGTCGGT GACAGAAG-3' | | 750 nM |
| STAT5B R | 5'-GGCTCTGCAAAA GCATTGTC-3' | | 750 nM |
| STAT5B P | 5'-CAGCCAGGACAA CAATGCGACGG-3' | 5'-[6~FAM]3'-[TAMRA~6~FAM] | 250 nM |
| BCR-ABL F (ENF 501) | 5'-TCCGCTGACCAT CAATAAGGA-3' | | |
| BCR-ABL R (ENR 561) | 5'-CACTCAGACCCT GAGGCTCAA-3' | | |
| BCR-ABL P (ENP 541) | 5'-CCCTTCAGCGGC CAGTAGCATCTGA-3' | 5'-[6~FAM]3'-[TAMRA~6~FAM] | |
| ABL F | 5'-TGGAGATAACAC TCTAAGCATAACTAA AGG-3' | | |
| ABL R | 5'-GATGTAGTTGCT TGGGACCCA-3' | | |
| ABL P | 5'-CCATTTTGGTTT GGGCTTCACACCAT T-3' | 5'-[6~FAM]3'-[TAMRA~6~FAM] | |

| b Name | Primer sequences | Conc |
|---|---|---|
| STAT5A F | 5'-CGAGTGCAGTGG TGAGATCC-3' | 750 nM |
| STAT5A R | 5'-TCCTCTGTCACG GACTCTGC-3' | 750 nM |
| PPARγ F | 5'-AGCTCCGTGGAT CTCTCCGT-3' | 650 nM |

TABLE 2-continued

Primers and probes used for RT-qPCR

| | | |
|---|---|---|
| PPARγ R | 5'-CATGAGGGAGTT GGAAGGCTCT-3' | 650 nM |
| CD36 F | 5'-TTGGCCAAGCTA TTGCGACA-3' | 750 nM |
| CD36 R | 5'-GCAAAGGCATTG GCTGGAAG-3' | 750 nM |
| hOCT1 F | 5'-CTGAGCTGTACC CCACATTCG-3' | 750 nM |
| hOCT1 R | 5'-CCAACACCGCAA ACAAAATGA-3' | 750 nM |
| MDR1 F | 5'-AGACATGACCAG GTATGCCTA-3' | 750 nM |
| MDR1 R | 5'-AGCCTATCTCCT GTCGCATTA-3' | 750 nM |
| SirT1 F | 5'-GATGACGATGAC AGAACGTCACA-3' | 900 nM |
| SirT1 R | 5'-GGATCGGTGCCA ATCATGAG-3' | 900 nM |
| STAT3 F | 5'-ACCTGCAGCAAT ACCATTGAC-3' | 750 nM |
| STAT3 R | 5'-AAGGTGAGGGAC TCAAACTGC-3' | 750 nM |
| ALOX5 F | 5'-CACATGTTCCAG TCTTCTTGGA-3' | 650 nM |
| ALOX5 R | 5'-ATGACCCGCTCA GAAATAGTGT-3' | 650 nM |
| PML F | 5'-TGCCAGTGTACG TCCTCTCC-3' | 600 nM |
| PML R | 5'-AGCCAACCTTGC CTCCTTCC-3' | 600 nM |

FAM: 6-carboxyfluorescein ester,
HEX: hexachloro fluorescein,
TAMRA: tetramethyl-6-carboxyrhodamine,
TAMRA: tetramethyl-6-carboxyrhodamine,
BHQ1: Black Hole Quencher,
Conc: concentration.

Example 8

Figure 9:
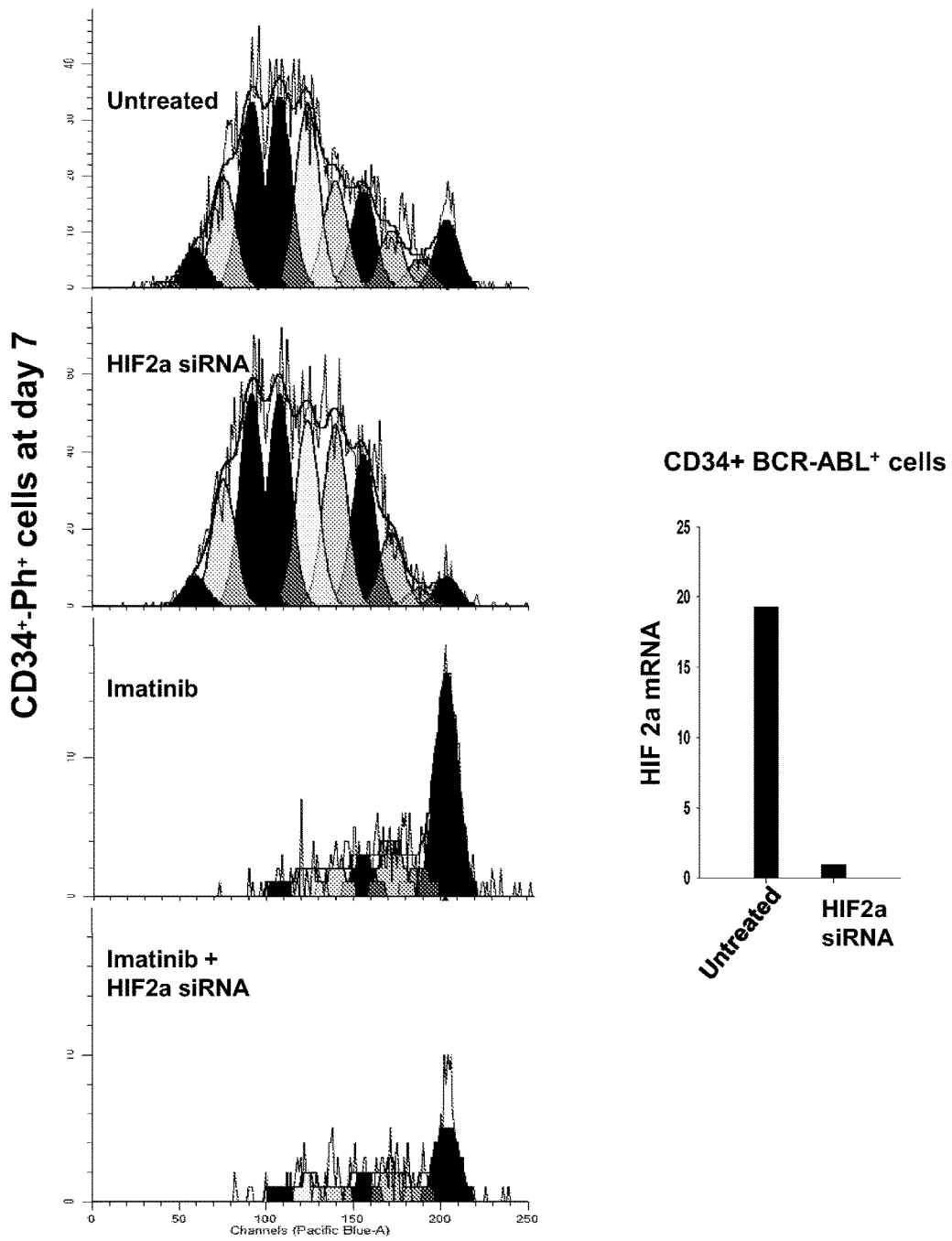
FIG. 9 shows quiescent CML stem cell (LSC) purging by HIF 2a suppression.

Studies were performed to show that STAT5 downregulation decreases the abnormally high expression of the transcription factor HIF 2a, resulting in quiescent CML stem cell (LSC) purging, when combined with Imatinib. HIF 2a siRNA was used to inhibit expression in CD34+ stem cells, alone and in combination with Imatinib. The results at day 7 are shown in FIG. 9, indicating that the combination of HIF 2a inhibition and Imatinib caused significant erosion of stem cells. Since LSCs are dependent on HIF 2a (regulated by STAT5), suppression of HIF 2a by STAT5 inhibitors (e.g., PPAR agonists, such as pioglitazone) induces proliferation of LSCs, and potentiates the effect of Imatinib therapy.

Example 9

The following studies were performed to evaluate whether targeting STAT5 expression with pioglitazone impacted clonogenic activity of Chronic Myelogenous Leukemia (CML) cells in vitro, resulting in molecular response improvement in vivo.

Patients and Methods

Preliminary in vitro studies tested the ability of pioglitazone to impact viability and clonogenicity of CD34$^+$ primary cells from CML patients. Clonogenic and LTC-IC studies were conducted. Cultivated Ph$^+$-CD34$^+$ cells were characterized by facs and analyzed by CSFE assay. BCR-ABL and STAT5 expression were quantified by real time PCR. Control experiments were conducted using lentiviral vectors and siRNA assay for Stat5 and PPAR-γ.

CML patients were eligible in the ACTIM trial (EudraCT 2009-011675-79) if they were treated by imatinib for at least 2 years, with a stable daily dose for at least 3 months, and in major molecular response without having achieved CMR4.5 (defined by a BCR-ABL/ABL IS ratio ≤0.0032%). After inclusion, patients received imatinib (no dose modification) and started pioglitazone (Actos®) 30 mg/d during 2 months and 45 mg/d thereafter for 12 months. BCR-ABL transcript level was monitored every 3 months during the study period. Primary objective was the proportion of patients achieving a confirmed undetectable level of BCR-ABL transcript. Secondary objectives included cumulative incidence of CMR4.5 and safety. A companion biologic study evaluated imatinib through levels, STAT5 expression in bone marrow at baseline, months 6 and 12 and clonogenic activity of bone marrow mononuclear cells at baseline, months 6 and 12.

Results

From the in vitro studies it was first demonstrated that pioglitazone at pharmacological doses inhibited cell growth of the Bcr-Abl positive cell line K562 through the activation of the PPAR-γ/STAT5 pathway. It was next shown that PPAR-γ/STAT5 pathway induced a clonogenic defect in CD34+ cells from CML patients. Moreover, the activation of the PPAR-γ/STAT5 pathway also induced a clonogenic and a proliferative defect in CML LTC-IC. It was then confirmed that imatinib induced a selection of insensitive quiescent CML cells and showed that this effect was abrogated by the activation of the PPAR-γ/STAT5 pathway.

Twenty-seven patients were enrolled in the clinical trial and 24 were evaluable (1 was excluded in CMR4.5, 1 patient was not in MMR and 1 patient had consent withdrawal). Median age was 61.6 years (24.1-79) and median follow-up after inclusion was 13 months (9.8-21). All evaluable patients started pioglitazone as planned. Seven patients (29.2%) discontinued pioglitazone before 12 months, 6 following investigator decision after the warning of the French ministry of health regarding the risk of bladder cancer, and 1 after its own decision. No patient discontinued due to adverse events. Discontinuations occurred between month 3 and month 9. Median duration of pioglitazone therapy was 11.2 months (2.6-15.4) median daily dose was 39.9 mg. Levels of imatinib were not significantly impacted before (median 850 ng/ml) and after (median 927 ng/ml) pioglitazone initiation (p=ns), indicating lack of interaction. Main adverse events were weight gain and worsening fluid retention in 3 patients. Three patients (14%) obtained a confirmed undetectable level of BCR-ABL transcript. The one year cumulative incidence of CMR4.5 was 57%. STAT5 mRNA quantification was significantly diminished in patient samples at M6 and M12 compared to the baseline values and a reduction of the clonogenic potential was also observed in bone marrow cells at M6 and M12. "Control patients" with similar characteristic were collected (n=20). None of these patients obtained a confirmed CMR and the cumulative incidence of CMR4.5 in this control group was 27%, as compared to 57% in the pioglitazone group (p=0.02).

Conclusion

The in vivo study extended previous in vitro results showing that PPAR-γ agonists resulted in STAT5 down regulation in CML CD34+ cells and preferentially reduced their clonogenic and long term potency in CFCs and LTC-IC assays. Specifically, the study demonstrated that these effects translate in vivo by the achievement of MMR in more than half of the patients treated with the combination of pioglitazone and imatinib, suggesting that it may be possible to target quiescent CML cells in vivo and supporting the concept of stem cell pool erosion.

We claim:

1. A method of preventing hematologic cancer relapse in a patient comprising:
   (A) administering to the patient an effective amount of an anti-cancer agent until a stable cumulative incidence of response in the patient is achieved, wherein the anti-cancer agent is a tyrosine kinase inhibitor (TKI) that inhibits phosphorylation of BCR-ABL selected from the group consisting of imatinib, dasatinib, nilotinib, bosutinib, and ponatinib; and
   (B) administering to the patient an effective amount of a peroxisome proliferator-activated receptor (PPARγ) agonist, wherein the PPARγ agonist is a thiazolidinedione that inhibits transcription of Signal Transducer and Activator of Transcription 5 (STAT5).

2. The method according to claim 1, wherein the response is selected from the group consisting of complete hematological remission (CHR), major cytological remission (MCR), complete cytological remission (CCR), major molecular remission (MMR) and complete molecular remission (CMR).

3. The method according to claim 1, wherein the TKI is administered for at least 3 months prior to administration of the PPARγ agonist.

4. The method according to claim 3, wherein the PPARγ agonist is administered for 2-12 months concurrently with the TKI.

5. The method according to claim 4, wherein administration of the TKI is continued after administration of the PPARγ agonist is discontinued.

6. The method according to claim 1, wherein the thiazolidinedione is selected from the group consisting of pioglitazone, rosiglitazone, troglitazone, englitazone, ciglitazone and netoglitazone.

7. The method according to claim 1, wherein the thiazolidinedione compound is pioglitazone.

8. The method according to claim 1, wherein the patient has leukemia.

9. The method according to claim 8, wherein the patient has chronic myeloid leukemia (CML) or acute myeloid leukemia.

10. The method according to claim 9, wherein the leukemia is CML.

11. The method according to claim 1, wherein the TKI is imatinib.

12. The method according to claim 1, wherein the PPARγ agonist is administered at a dose of about 15-60 mg/day.

13. The method according to claim 1, wherein the PPARγ agonist is administered at a dose of about 30-50 mg/day.

14. The method according to claim 1, wherein the TKI is administered at a dose of about 300-800 mg/day.

15. The method according to claim 1, wherein the TKI is administered at a dose of about 300-400 mg/day.

16. A method of preventing relapse of a myeloid cancer comprising:
(A) administering to a patient with a myeloid cancer, about 300-400 mg/day of a tyrosine kinase inhibitor (TKI) that inhibits phosphorylation of BCR-ABL selected from the group consisting of imatinib, dasatinib, nilotinib, bosutinib, and ponatinib until a stable cumulative incidence of response in the patient is achieved; and
(B) administering to the patient about 30-50 mg/day of a thiazolidinedione that inhibits transcription of Signal Transducer and Activator of Transcription 5 (STAT5).

17. The method according to claim 16, wherein the thiazolidinedione is selected from the group consisting of pioglitazone, rosiglitazone, troglitazone, englitazone, ciglitazone and netoglitazone.

18. The method according to claim 17, wherein the thiazolidinedione is administered for about 2-12 months until a CMR is achieved.

19. The method according to claim 17, wherein the thiazolidinedione is administered at a dose of about 30 mg/day for 2 months and about 45 mg/day thereafter for a total of 12 months.

20. A method of preventing relapse of chronic myelogenous leukemia (CML) characterized by t(9:22)(q34;q11) reciprocal translocation (der22 or Ph+ chromosome) and BCR-ABL fusion protein expression, the method comprising,
(A) administering to a patient with CML about 300-400 mg/day of a TKI that inhibits phosphorylation of BCR-ABL selected from the group consisting of imatinib, dasatinib, nilotinib, bosutinib, and ponatinib until a stable cumulative incidence of response in the patient is achieved; and
(B) administering to the patient about 30-50 mg/day of a thiazolidinedione that inhibits transcription of STAT5 until a complete molecular response (CMR) is achieved.

21. The method according to claim 20, wherein the thiazolidinedione is selected from the group consisting of pioglitazone, rosiglitazone, troglitazone, englitazone, ciglitazone and netoglitazone.

22. The method according to 20, wherein the TKI is imatinib.

23. The method according to claim 20, wherein the glitazone is pioglitazone.

24. The method according to claim 17, wherein the thiazolidinedione is pioglitazone.

25. The method according to claim 17, wherein the TKI is imatinib.

26. The method of claim 1, wherein
the TKI is imatinib
and the thiazolidinedione is pioglitazone.

27. The method of claim 16, wherein
the TKI is imatinib
and the thiazolidinedione is pioglitazone.

28. The method of claim 20, wherein
the TKI is imatinib
and the thiazolidinedione is pioglitazone.

* * * * *